US012606523B2

(12) United States Patent
Vadodaria et al.

(10) Patent No.: US 12,606,523 B2
(45) **Date of Patent: *Apr. 21, 2026**

(54) DEUTERATED ORGANIC COMPOUNDS AND USES THEREOF

(71) Applicant: ENGRAIL THERAPEUTICS, INC., San Diego, CA (US)

(72) Inventors: Krishna Vadodaria, San Diego, CA (US); Kimberly Vanover, Tulsa, OK (US); Jordi Serrats, San Diego, CA (US); Vikram Sudarsan, San Diego, CA (US); David Garvey, Dover, MA (US)

(73) Assignee: ENGRAIL THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/763,819

(22) Filed: Jul. 3, 2024

(65) Prior Publication Data

US 2025/0011280 A1 Jan. 9, 2025

Related U.S. Application Data

(63) Continuation of application No. PCT/US2023/010055, filed on Jan. 3, 2023.

(60) Provisional application No. 63/384,988, filed on Nov. 25, 2022, provisional application No. 63/394,565, filed on Aug. 2, 2022, provisional application No. 63/345,002, filed on May 23, 2022, provisional application No. 63/314,466, filed on Feb. 27, 2022, provisional application No. 63/296,137, filed on Jan. 3, 2022.

(51) Int. Cl.

| | |
|---|---|
| ***C07D 207/14*** | (2006.01) |
| ***A61K 31/40*** | (2006.01) |
| ***A61P 25/18*** | (2006.01) |
| ***A61P 25/24*** | (2006.01) |

(52) U.S. Cl.

CPC ............ *C07D 207/14* (2013.01); *A61K 31/40* (2013.01); *A61P 25/18* (2018.01); *A61P 25/24* (2018.01)

(58) Field of Classification Search

CPC .................................................... C07D 207/14

See application file for complete search history.

(56) References Cited

U.S. PATENT DOCUMENTS

| | | | |
|---|---|---|---|
| 4,197,243 A | 4/1980 | Murakami et al. | |
| 4,210,660 A * | 7/1980 | Takashima | C07D 207/14 548/557 |
| 5,624,687 A | 4/1997 | Yano et al. | |
| 6,436,441 B1 | 8/2002 | Sako et al. | |
| 6,872,405 B2 | 3/2005 | Takaishi et al. | |
| 12,365,650 B2 | 7/2025 | Vadodaria et al. | |
| 2019/0328745 A1 | 10/2019 | Vanover et al. | |
| 2019/0343827 A1 | 11/2019 | Bunt | |
| 2021/0017160 A1 | 1/2021 | Lee et al. | |
| 2025/0011279 A1 | 1/2025 | Vadodaria et al. | |
| 2025/0091990 A1 | 3/2025 | Vadodaria et al. | |

FOREIGN PATENT DOCUMENTS

| | | |
|---|---|---|
| CN | 104744333 A | 7/2015 |
| WO | WO 94/10174 A1 | 5/1994 |
| WO | WO 2020/176597 A1 | 9/2020 |
| WO | WO 2023/130117 A1 | 7/2023 |
| WO | WO 2025/010255 A2 | 1/2025 |
| WO | WO 2025/010259 A2 | 1/2025 |
| WO | WO 2025/010266 A1 | 1/2025 |

OTHER PUBLICATIONS

Tung ("Deuterium medicinal chemistry comes of age," Future Med. Chem. 2016, 8, 5, 491-494) (Year: 2016).*

Admon, R. et al., "Dopaminergic enhancement of striatal response to reward in major depression," HHS Public Access, Author manuscript, available in PMC 2018, 16 pages, face of article states: Published in final edited form as: *Am J Psychiatry*. 2017; 174(4): 378-386, doi:10.1176/appi.ajp.2016.16010111.

Bishara, D. et al., "Upcoming Agents for the Treatment of Schizophrenia," Drugs, 2008, 68 (16), 2269-2292.

CAS Registry No. 3067217-43-7, document states Entered STN: Jan. 13, 2025, 1 page.

Celada, P. et al., "Serotonin 5-HT1A Receptors as Targets for Agents to Treat Psychiatric Disorders: Rationale and Current Status of Research," CNS Drugs, 2013, 27, 703-716.

CN 104744333 A published Jul. 1, 2015, and English machine translation thereof (on last page), 4 pages total.

Curran, M. et al., "Amisulpride," Drugs, 2001, 61 (14), 2123-2150.

Di Martino, R. et al., "Deuterium in drug discovery: progress, opportunities and challenges," Nature Reviews Drug Discovery, 2023, 22, 562-584.

Dyck, L. et al., "Effects of Deuterium Substitution on the Catabolismof β-Phenylethylamine: An In Vivo Study," Journal of Neurochemistry, 1986, 46 (2), 399-404.

English translation (20 pages) of Nakayama, K. et al., "Examination of clinical usability of nemonapride on postpsychotic depression," Clinical Psychiatry, 1995, 24 (5), 595-604.

Ford, C., "The Role of D2-Autoreceptors in Regulating Dopamine Neuron Activity and Transmission," HHS Public Access, Author manuscript, available in PMC 2015, 21 pages, face of article states: Published in final edited form as: *Neuroscience*. 2014, 282: 13-22, doi:10.1016/j.neuroscience.2014.01.025.

Furrow, M. et al., "Protecting deuterated drugs," Intellectual Property Magazine, dated 2018, 35-36, retrieved on Jan. 3, 2025, from: https://www.venable.com/-/media/files/publications/2018/02/protecting-deuterated-drugs.pdf?rev=e1b96c24e5ea433c89765760321b71ad&hash=9CF3EC763FA6B87D49C9125BBD18F522.

(Continued)

*Primary Examiner* — Yong S. Chong

(74) *Attorney, Agent, or Firm* — Hoxie & Associates LLC

(57) ABSTRACT

Provided are compounds of Formula I, described herein, processes for their preparation, their use as pharmaceuticals, and pharmaceutical compositions comprising them and intermediates used in their preparation. Compounds of Formula I are useful, for instance, in modulating dopamine neurotransmission and treating disorders that may benefit from the same, such as schizophrenia and depression.

17 Claims, 13 Drawing Sheets

(56) References Cited

OTHER PUBLICATIONS

Garcia-Garcia, A. et al., "5-$HT_{1A}$ receptors in mood and anxiety: recent insights into autoreceptor versus heteroreceptor function," NIH Public Access, Author manuscript, available in PMC 2015, 24 pages, face of article states: Published in final edited form as: *Pyschopharmacology* (*Berl*). 2014, 231(4): 623-636, doi: 10.1007/s00213-013-3389-x.
Harbeson, S. et al., "Deuterium Medicinal Chemistry: A New Approach to Drug Discovery and Development," Medchem News, 2014, No. 2, 8-22.
Hatano, K. et al., "Synthesis of ω-[$^{18}$F]Flouroalkyl Analogs of YM-09151-2 for the Measurement of $D_2$-Dopamine Receptors with PET," Applied Radiation and Isotopes, 1990, 41 (6), 551-555.
Hernandes, M. et al., "Halogen Atoms in the Modern Medicinal Chemistry: Hints for the Drug Design," Current Drug Targets, 2010, 11, 12 pages.
Higuchi, S. et al., "Comparative pharmacokinetics of a new benzamide neuroleptic drug in rats, dogs and monkeys using a stable isotope technique," Xenobiotica, 1986, 16 (1), 79-86.
Hoang, C. et al., "3-Aminopyrrolidines from α-Aminoacids: Total Synthesis of (+)-Nemonapride from D-Alanine," Journal of Organic Chemistry, 2008, 73, 1162-1164.
Iwanami, S. et al., "Synthesis and Neuroleptic Activity of Benzamides, cis-N-(1-Benzyl-2-methylpyrrolidin-3-yl)-5-chloro-2-methoxy-4-(methylamino)benzamide and Related Compounds," Journal of Medicinal Chemistry, 1981, 24, 1224-1230.
Kurczab, R. et al., "The Significance of Halogen Bonding in Ligand-Receptor Interactions: The Lesson Learned from Molecular Dynamic Simulations of the $D_4$ Receptor," Molecules, 2020, 25, 91, doi:10.3390/molecules25010091, 14 pages.
Kusumi, I. et al., "Psychopharmacology of atypical antipsychotic drugs: From the receptor binding profile to neuroprotection and neurogenesis," Psychiatry and Clinical Neurosciences, 2015, 69, 243-258.
Lavergne, F. et al., "A new strategy for antidepressant prescription," Frontiers in Neuroscience, 2010, 4, Article 192, 13 pages, doi: 10.3389/fnins.2010.00192.
Li, P. et al., "Dopamine Targeting Drugs for the Treatment of Schizophrenia: Past, Present and Future," Current Topics in Medicinal Chemistry, 2016, 16, 3385-3403.
Ly, C. et al., "Psychedelics Promote Structural and Functional Neural Plasticity," Cell Reports, 2018, 23, 3170-3182.
Marseille, E. et al., "The cost-effectiveness of MDMA-assisted psychotherapy for the treatment of chronic, treatment resistant PTSD," PLoS ONE, 2020, 15 (10): e0239997, 14 pages, https://doi.org/10.1371/journal.pone.0239997.
Mckeage, K. et al., "Amisulpride," CNS Drugs, 2004, 18 (13), 933-956.
Mishra, A. et al., "Physiological and Functional Basis of Dopamine Receptors and Their Role in Neurogenesis: Possible Implication for Parkinson's disease," Journal of Experimental Neuroscience, 2018, 12, 8 pages, doi: 10.1177/1179069518779829.
Nakayama, K. et al., "Examination of clinical usability of nemonapride on postpsychotic depression," Clinical Psychiatry, 1995, 24 (5), 595-604.
Neuroperspective, "Psychedelics, Epilepsy, Rett Syndrome," dated Summer Jul.-Sep. 2022, No. 319-321, ISSN 1537-6346, pp. 3-39 and 66.
Newman-Tancredi, A., "Novel antipsychotics activate recombinant human and native rat serotonin 5-HT1A receptors: affinity, efficacy and potential implications for treatment of schizophrenia," International Journal of Neuropsychopharmacology, 2005, 8, 341-356.
Newman-Tancredi, A., "Biased agonism at serotonin 5-$HT_{1A}$ receptors: preferential postsynaptic activity for improved therapy of CNS disorders," Neuropsychiatry, 2011, 1 (2), 149-164.
Noda-Saita, K. et al., "Dopamine D4-like Binding Sites Labeled by [$^3$H]Nemonapride Include Substantial Serotonin 5-HT2A Receptors in Primate Cerebral Cortex," Biochemical and Biophysical Research Communications, 1999, 255, 367-370.
Pubchem CID 4452, Modify date listed as: Feb. 24, 2023, 2 pages, retrieved by USPTO as ISA in International Application No. PCT/US2023/010055 on Mar. 3, 2023, from: https://pubchem.ncbi.nlm.nih.gov/compound/4452.
Pubchem SID 85789047, Modify date listed as: Mar. 9, 2010, 8 pages, retrieved by USPTO as ISA in International Application No. PCT/US2023/010050 on Feb. 27, 2023, from: https://pubchem.ncbi.nlm.nih.gov/substance/85789047.
Rao, N. et al., "Deuterated Drugs," Pharmaceutical Chemistry Journal, 2022, 55 (12), 1372-1377.
Schotte, A. et al., "In Vitro Receptor Binding and In Vivo Receptor Occupancy in Rat and Guinea Pig Brain: Risperidone Compared with Antipsychotics Hitherto Used," Japanese Journal of Pharmacology, 1995, 69, 399-412.
Seeman, P. et al., "Deriving the therapeutic concentrations for clozapine and haloperidol: The apparent dissociation constant of a neuroleptic at the dopamine $D_2$ or $D_4$ receptor varies with the affinity of the competing radioligand," European Journal of Pharmacology, 1995, 291, 59-66.
Tamazawa, K. et al., "Synthesis of [Carbonyl-$^{14}$C]- and (Methoxy-$d_3$)-labeled N-[(2RS,3RS)-1-Benzyl-2-methyl-3-pyrrolidinyl]-5-chloro-2-methoxy-4-(methylamino) Benzamide (YM-09151-2), A New Potent Neuroleptic Agent," Journal of Labelled Compounds and Radiopharmaceuticals, 1984, XXI (5), 441-453.
Tung, R., "The Development of Deuterium-Dontaining Drugs," cited in U.S. Appl. No. 18/761,559, 5 pages, front page states: Innovations in Pharmaceutical Technology, 32 (32), 24-28, dated 2010.
Wang, P. et al., "Use of antipsychotics in the treatment of depressive disorders," Shanghai Archives of Psychiatry, 2013, 25 (3), 134-140.
Wang, X-M. et al., "Effect of deuteration on the single dose pharmacokinetic properties and postoperative analgesic activity of methadone," HHS Public Access, Author manuscript, available in PMC 2023, 26 pages, face of article states: Published in final edited form as: *Drug Metab Pharmacokinet*. 2022; 47: 100477, doi:10.1016/j.dmpk.2022.100477.
Zhang, G. et al., "The role of serotonin 5-$HT_{2A}$ receptors in memory and cognition," Frontiers in Pharmacology, 2015, 6, Article 225, 17 pages, doi: 10.3389/fphar.2015.00225.
Chen, J. et al., "Second-generation antipsychotics in major depressive disorder: update and clinical perspective," Current Opinion in Psychiatry, 2011, 24, 10-17.
Foster, A., "Deuterium Isotope Effects in the Metabolism of Drugs and Xenobiotics: Implications for Drug Design," Advances in Drug Research, 1985, 14, 1-40.
Extended European Search Report for European Patent Application No. 23735189.5 dated Jun. 16, 2025, 7 pages.
Li, G. et al., "Effective Method for Synthesis of Antipsychotics (2S,3S)-Nemonapride," Chinese Journal of Organic Chemistry, 2016, 36, 2157-2161.

* cited by examiner

DEUTERATED ORGANIC COMPOUNDS AND USES THEREOF

CROSS REFERENCE TO RELATED APPLICATIONS

This application is a continuation of International Application No. PCT/US2023/010055 filed Jan. 3, 2023, which claims priority to U.S. Provisional Application No. 63/296,137 filed Jan. 3, 2022, U.S. Provisional Application No. 63/314,466 filed Feb. 27, 2022, U.S. Provisional Application No. 63/345,002 filed May 23, 2022, U.S. Provisional Application No. 63/394,565 filed Aug. 2, 2022, and U.S. Provisional Application No. 63/384,988 filed Nov. 25, 2022, the contents of each of which are hereby incorporated by reference in their entireties.

FIELD

Provided are compounds of Formula I, described below, processes for their preparation, their use as pharmaceuticals, and pharmaceutical compositions comprising them and intermediates used in their preparation. Compounds of Formula I are useful, for instance, in modulating dopamine neurotransmission and treating disorders that may benefit from the same, such as schizophrenia and depression.

BACKGROUND

Dopamine is involved in a variety of central nervous system functions, including voluntary movement, feeding, affect, reward, sleep, attention, working memory, and learning. Dopaminergic dysfunction can lead to diseases such as schizophrenia and depression.

When released from presynaptic terminals, dopamine activates members of a family of G protein-coupled dopamine receptors D1-D5. Dopamine receptors (D1-D5) are divided into two groups, the D1-like (D1 and D5) and the D2-like (D2, D3, and D4). Activation of D1-like receptors activates adenylyl cyclase and increases cAMP levels. D2-like receptors are inhibitory. Activation of D2-like receptors inhibits activation of adenylyl cyclase.

D1-like receptors are found postsynaptically on dopamine-receptive cells, while D2-like dopamine receptors are expressed both postsynaptically on dopamine target cells and presynaptically on dopaminergic neurons.

Antipsychotics are used to manage psychosis, in particular schizophrenia. A hallmark of antipsychotics is D2 receptor antagonism. D2 receptor antagonism is effective in reducing positive symptoms of schizophrenia (for instance, hallucinations and delusions), but often also produces extrapyramidal side effects, including parkinsonism, akathisia, and tardive dyskinesia, increases prolactin, and may exacerbate negative symptoms of schizophrenia (for instance, loss of interest and motivation in life and activities, social withdrawal, and anhedonia). Many psychotic patients also suffer from depression, which may be left untreated by current medications.

In addition to effects on dopamine receptors, such as D2, D3, and D4, antipsychotics may also have effects on serotonin receptors, such as 5-HT1A, 5-HT2A, 5-HT2C, 5-HT6, and 5-HT7. Interacting with dopamine and serotonin receptors may be beneficial, for instance, resulting in reduced extrapyramidal motor side effects (EPS) liability. However, multi-target drugs may also result in undesirable off-target side effects.

Because imbalances in dopamine can lead to a variety of disorders and current medications may not be able to effectively modulate dopamine levels and may have undesirable side effects, new compounds that can modulate dopamine neurotransmission are needed, as are methods of treating diseases that involve imbalances in dopamine.

BRIEF SUMMARY

Provided is a compound of Formula I:

Formula I

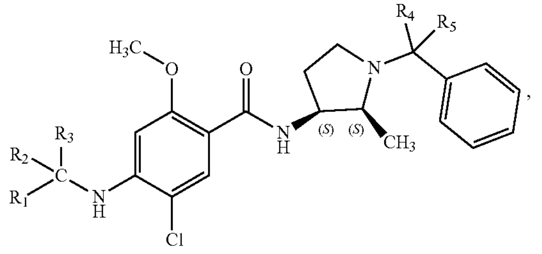

wherein:

$R_1$, $R_2$, $R_3$, $R_4$, and $R_5$ are independently selected from H and D; and at least one of $R_1$, $R_2$, and $R_3$ is D;

in free or salt form.

Further provided are pharmaceutical compositions comprising compounds of Formula I, processes for preparing compounds of Formula I, and pharmaceutical uses of compounds of Formula I, for instance, as an anti-anhedonic agent and to treat schizophrenia and depression.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

DETAILED DESCRIPTION

Figure 1:
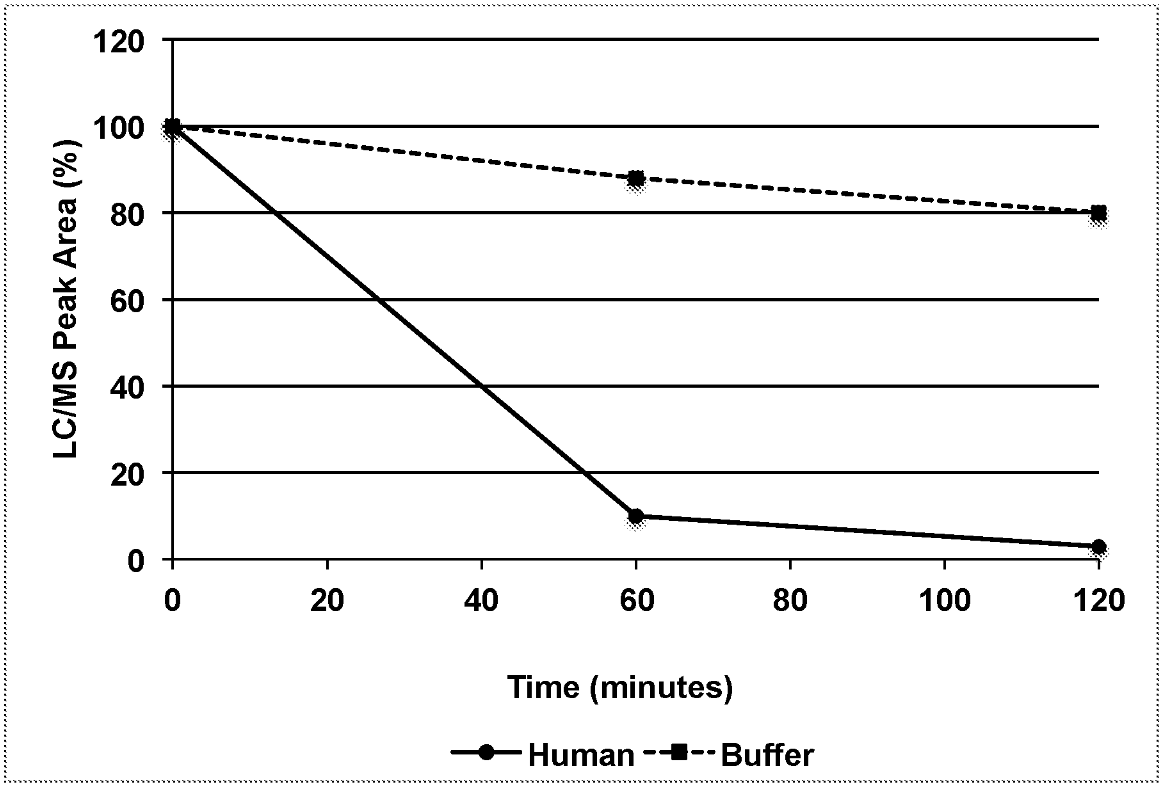
FIG. 1 shows disappearance of the compound of Example 1 (A1) in human hepatocytes.

The following description of the preferred embodiment(s) is merely exemplary in nature and is in no way intended to limit the invention, its application, or uses.

In the event of a conflict in a definition in the present disclosure and that of a cited reference, the present disclosure controls.

D2- and D3-receptors are expressed both postsynaptically on dopamine target cells and presynaptically on dopamine neurons. Dopamine receptors are mainly located on non-dopamine neurons. Dopamine receptors on dopamine neurons are called autoreceptors. Autoreceptors contribute to regulating dopamine neuron activity and controlling the synthesis, release, and uptake of dopamine.

Presynaptic D2-like dopamine autoreceptors regulate dopamine release. A low dose of a D2-like receptor antagonist may preferentially block presynaptic autoreceptors and increase dopamine release, while a high dose may block postsynaptic receptors and decrease dopamine neurotransmission. Relatively high occupancy of D2-like receptors has been associated with antipsychotic effects, while lower occupancy has been associated with antidepressant effects.

Anhedonia is a core symptom of major depressive disorder (MDD) and is associated with inadequate response to approved selective serotonin reuptake inhibitors (SSRIs) and serotonin norepinephrine reuptake inhibitors (SNRIs) and psychotherapy (e.g., cognitive behavioral therapy (CBT)) and neurostimulation (e.g., transcranial magnetic stimulation (TMS)). There remains a need for effective treatment of MDD characterized by anhedonia. Despite a range of available therapies, up to 50% of people suffering from MDD fail to respond to treatments, and only about 30% of patients fully recover after receiving currently available antidepressants and treatment outcomes are even poorer for MDD individuals with anhedonia.

Depletion of dopamine/catecholamines induces symptoms of depression and anhedonia. Increasing dopamine neurotransmission can alleviate symptoms of depression and anhedonia. However, while a high dose of a dopamine D2/D3 agonist may activate dopamine post-synaptic receptors, it can also be poorly tolerated (e.g., nausea/vomiting). Low dose of a dopamine D2/D3 receptor antagonist may preferentially block pre-synaptic dopamine autoreceptors and increase dopamine release without being poorly tolerated.

Besides MDD, anhedonia also plays a role in bipolar disorder, schizophrenia, post-traumatic stress disorder, and substance use disorder. Despite its role in many disorders, there are no approved medications to treat anhedonia.

The IUPAC name of nemonapride is (±)-cis-N-(1-Benzyl-2-methylpyrrolidin-3-yl)-5-chloro-2-methoxy-4-methylaminobenzamide. Nemonapride is described in U.S. Pat. No. 4,210,660 as a strong central nervous system depressant, in particular a strong antipsychotic.

Nemonapride is a dopamine D2/D3/D4 receptor antagonist. Nemonapride is approved in Japan and South Korea for treatment of schizophrenia. Nemonapride is supplied as 3 mg and 10 mg tablets. The approved daily dose of nemonapride for schizophrenia is 9 to 36 mg given orally in divided doses after meals. The dose can be increased up to 60 mg daily.

The nemonapride prescribing information indicates that the elimination half-life when nemonapride 3 mg and 6 mg was administered orally to healthy adults was 2.3 to 4.5 hours. Urinary metabolites of nemonapride result from debenzylation and N-demethylation. See Emilace package insert.

In addition to being a dopamine D2/D3/D4 receptor antagonist, nemonapride is also a 5-HT1A agonist and has been reported to bind to 5-HT2A.

When a drug is used as a mixture of stereoisomers, it is not possible to predict what properties (e.g., biological target, pharmacokinetics) each stereoisomer has, especially a drug that has multiple biological targets.

Compounds of Formula I disclosed herein are selective D2/D3/D4 receptor antagonists. D2/D3/D4 postsynaptic receptor antagonism reduces psychosis, particularly in schizophrenia, by reducing dopamine neurotransmission. A low dose of a D2/D3/D4 receptor antagonist may selectively block presynaptic autoreceptors resulting in increased dopamine release and enhanced dopamine neurotransmission. Moreover, antagonism of D3 receptors can have important implications for diseases related to mesolimbic and mesocortical dopamine systems given the enrichment of D3 receptors in the ventral striatum, thalamus, hippocampus, and cortex, dopaminergic brain areas involved in decision making and reward processing, relative to antagonism of D2 receptors alone. Given that D3 receptors have a higher affinity for dopamine compared to D2 receptors, increased dopamine release may preferentially activate D3 receptors. Additionally, by selectively blocking D2-like receptors but not D1-like receptors, increased dopamine release by a low dose of a D2/D3/D4 receptor antagonist may preferentially activate postsynaptic D1-like receptors, enriched in cortex, thereby improving cognition and negative symptoms of schizophrenia. Antagonism of D4 receptors, enriched in the frontal cortex and amygdala, among other brain areas, may also play a role in emotion processing. Selective D2/D3/D4 receptor antagonists limit off target interactions. Off target interactions may contribute to side effects in drugs that are not as selective.

Pharmacokinetics of deuterated compounds disclosed herein are beneficial. The deuterated compound of Example 1 shows extended brain enrichment compared to plasma levels of the compound. The enrichment in the brain persists up to 24 hours. That feature allows for higher receptor occupancy with less frequent dosing and may be associated with fewer peripheral side effects. The brain:plasma exposure supports once-daily dosing. In contrast, nemonapride is taken in multiple doses per day.

Data in the examples indicate that D2/D3 receptor occupancy levels of the deuterated compound of Example 1 in anti-anhedonic range may be achieved with relatively low and once daily dosing.

Figure 9:
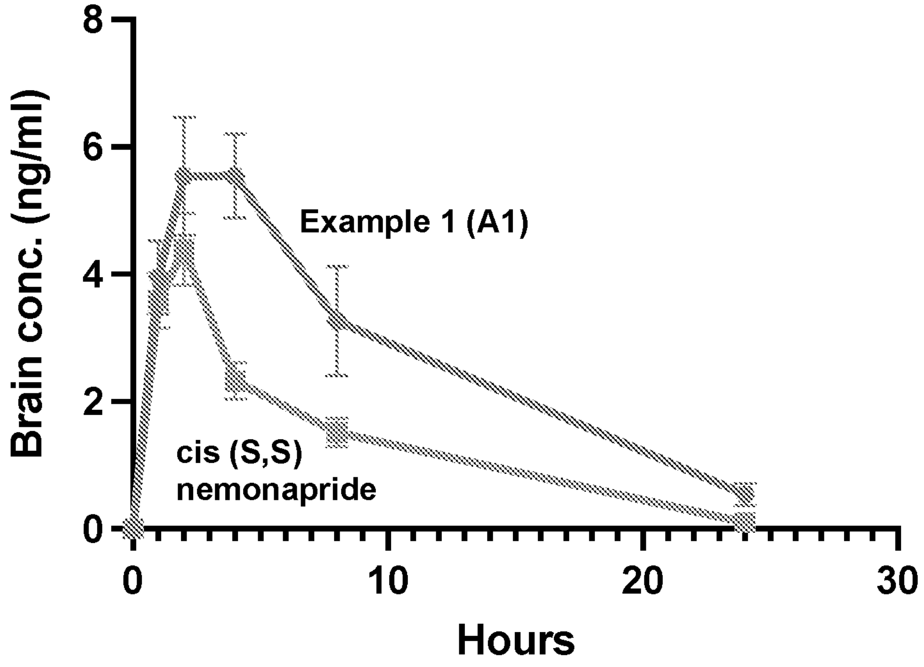
FIG. 9 shows average brain concentration (ng/ml) in rats of cis (S,S) nemonapride and the compound of Example 1 (A1) following single oral administration of 2.5 mg/kg.
Figure 10:
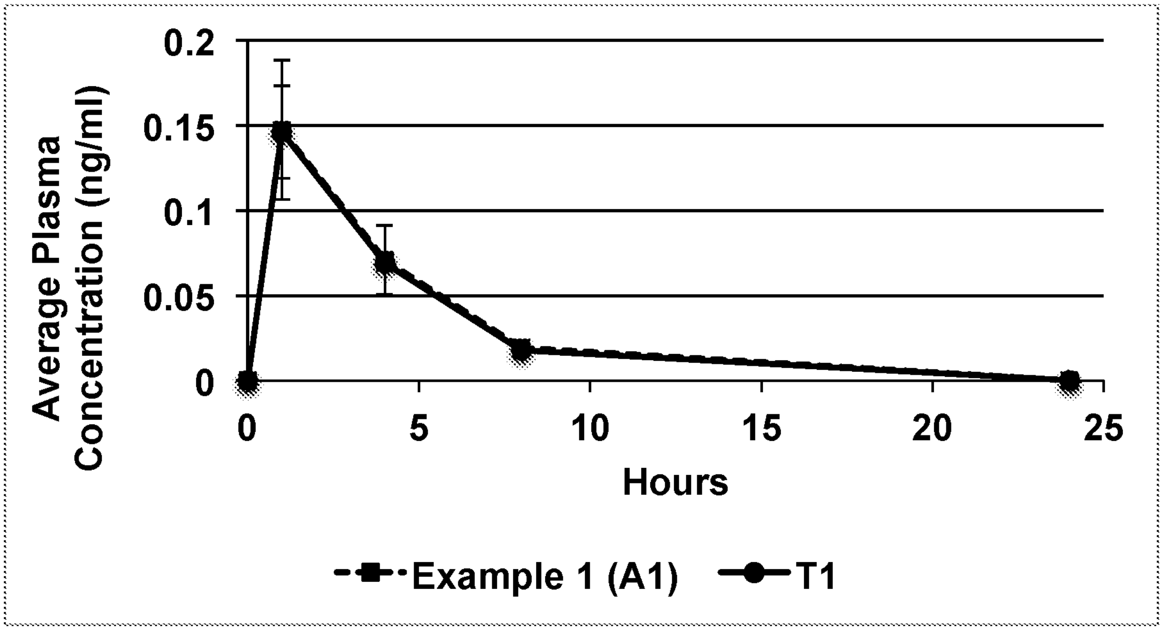
FIG. 10 shows average plasma concentration (ng/ml) in rats of T1 and the compound of Example 1 (A1) following single oral administration of 0.5 mg/kg.

In addition, Example 6 shows that a compound of Formula I (the deuterated compound of Example 1) has enriched and retained brain levels compared to its non-deuterated analog and higher receptor occupancy levels at 4, 8, and 24 hours. For instance, FIG. 9 shows that at 8 hours, brain levels of the compound of Example 1 (A1) are over double levels of cis (S,S) nemonapride measured. As discussed above, the deuterated compound of Example 1 also shows extended brain enrichment compared to plasma levels of the compound. Enriched brain levels, higher receptor occupancy levels, and extended brain enrichment compared to plasma levels are beneficial features that allow for higher and more sustained receptor occupancy with less frequent dosing and may be associated with fewer peripheral side effects. Receptor occupancy levels can be maintained in a desired range with a convenient dosing regime.

Further, Example 8 shows that a compound of Formula I (the deuterated compound of Example 1) has enriched and retained brain levels compared to another cis (S,S) nemonapride deuterated derivative.

Compounds that are D2/D3/D4 receptor antagonists modulate dopamine neurotransmission and are therefore useful in treating disorders involving dopamine signaling pathways, for instance, disorders involving D2, D3, and/or D4 receptors.

Provided is a compound of Formula I:

Formula I

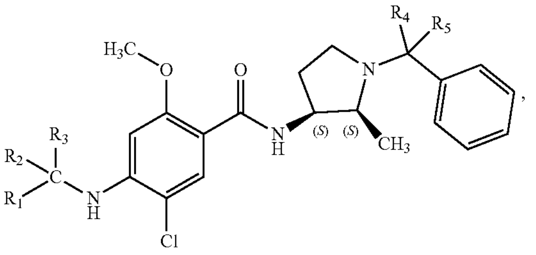

wherein:

$R_1$, $R_2$, $R_3$, $R_4$, and $R_5$ are independently selected from H and D; and at least one of $R_1$, $R_2$, and $R_3$ is D;

in free or salt form.

Further provided are compounds of Formula I as follows:

1.1 Formula I, wherein the compound is in pharmaceutically acceptable salt form.

1.2 Formula I, wherein the compound is in free form.

1.3 Any of Formula I, 1.1, or 1.2, wherein $R_1$, $R_2$, and $R_3$ are D.

1.4 Any of Formula I or 1.1-1.3, wherein $R_4$ and $R_5$ are D.

1.5 Any of Formula I or 1.1-1.4, wherein each of $R_1$, $R_2$, $R_3$, $R_4$, and $R_5$ are D.

1.6 Any of Formula I or 1.1-1.5, wherein the compound is:

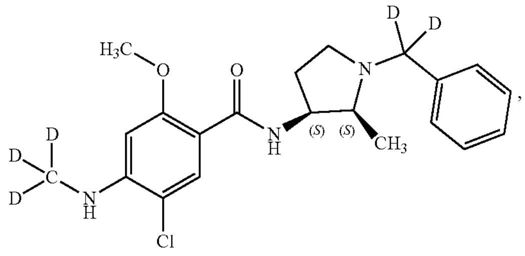

in free or salt form, e.g., in free or pharmaceutically acceptable salt form, e.g., in free form.

1.7 Any of Formula I or 1.1-1.6, wherein the designation of deuterium (i.e., D) at a position means that position has a significantly greater than natural abundance of deuterium at that position (e.g., greater than 0.1%, or greater than 0.5%, or greater than 1%, or greater than 5%). Any atom not designated as a particular isotope is present at natural isotopic abundance.

1.8 Any of Formula I or 1.1-1.7, wherein the compound, in free or salt form (e.g., pharmaceutically acceptable salt form), has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Formula I or 1.1-1.7, wherein the compound, in free or salt form (e.g., pharmaceutically acceptable salt form), has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%.

1.9 Any of Formula I or 1.1-1.8, wherein the compound is substantially stereoisomerically pure. For instance, wherein the compound has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the compound is substantially diastereomerically and/or enantiomerically pure, e.g., wherein the compound is substantially diastereomerically and enantiomerically pure.

1.10 Any of Formula I or 1.1-1.9, wherein the compound is substantially diastereomerically pure. For instance, wherein the compound has a diastereomeric excess of greater than 90%, e.g., a diastereomeric excess equal to or greater than 95%, e.g., a diastereomeric excess equal to or greater than 96%, e.g., a diastereomeric excess equal to or greater than 97%, e.g., a diastereomeric excess equal to or greater than 98%, e.g., a diastereomeric excess equal to or greater than 99%.

1.11 Any of Formula I or 1.1-1.10, wherein the compound is substantially enantiomerically pure. For instance, wherein the compound has an enantiomeric excess of greater than 90%, e.g., an enantiomeric excess equal to or greater than 95%, e.g., an enantiomeric excess equal to or greater than 96%, e.g., an enantiomeric excess equal to or greater than 97%, e.g., an enantiomeric excess equal to or greater than 98%, e.g., an enantiomeric excess equal to or greater than 99%.

1.12 Any of Formula I or 1.1-1.11, wherein the compound has the stereochemical configuration as shown in Formula I.

1.13 Any of Formula I or 1.1-1.12, wherein the compound is in a pharmaceutical composition with a pharmaceutically acceptable carrier. For instance, any of Formula I or 1.1-1.12, wherein an effective amount of the compound is in a pharmaceutical composition with a pharmaceutically acceptable carrier.

Further provided is a pharmaceutical composition (Composition 1) comprising a compound of Formula I (e.g., any of Formula 1.1-1.13):

Formula I

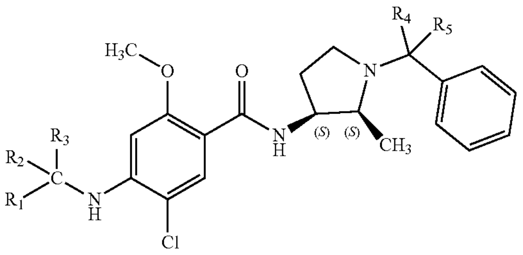, wherein:

$R_1$, $R_2$, $R_3$, $R_4$, and $R_5$ are independently selected from H and D; and at least one of $R_1$, $R_2$, and $R_3$ is D;

in free or pharmaceutically acceptable salt form.

Further provided is Composition 1 as follows:

1.1 Composition 1, wherein the composition comprises a pharmaceutically acceptable carrier.

1.2 Composition 1 or 1.1, wherein the composition comprises the compound, in free or pharmaceutically acceptable salt form, as described in any of Formula I or 1.1-1.13 vide supra.

1.3 Any of Composition 1, 1.1, or 1.2, wherein the compound is in free form.

1.4 Any of Composition 1 or 1.1-1.3, wherein the compound of Formula I is:

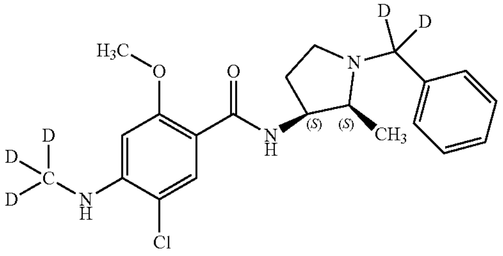

in free or pharmaceutically acceptable salt form, e.g., in free form.

1.5 Any of Composition 1 or 1.1-1.4, wherein the designation of deuterium (i.e., D) at a position means that position has a significantly greater than natural abundance of deuterium at that position (e.g., greater than 0.1%, or greater than 0.5%, or greater than 1%, or greater than 5%). Any atom not designated as a particular isotope is present at natural isotopic abundance.

1.6 Any of Composition 1 or 1.1-1.5, wherein the compound of Formula I, in free or pharmaceutically acceptable salt form, has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Composition 1 or 1.1-1.5, wherein the compound of Formula I, in free or pharmaceutically acceptable salt form, has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%.

1.7 Any of Composition 1 or 1.1-1.6, wherein the composition is in oral or parenteral dosage form, e.g., oral dosage form, for instance, a tablet, capsule, solution, or suspension, for instance, a capsule or tablet.

1.8 Any of Composition 1 or 1.1-1.7, wherein the composition comprises a therapeutically effective amount of the compound of Formula I, in free or pharmaceutically acceptable salt form, e.g., a therapeutically effective amount of the compound of Formula I, in free or pharmaceutically acceptable salt form, for the prophylaxis or treatment of a disorder disclosed herein, e.g., a therapeutically effective amount of the compound of Formula I, in free or pharmaceutically acceptable salt form, for use in any of the methods disclosed herein.

1.9 Any of Composition 1 or 1.1-1.8, wherein the composition is substantially free of any other stereoisomeric form of Formula I. For instance, any of Composition 1 or 1.1-1.8, wherein the composition is substantially free of any other diastereomeric and/or enantiomeric form of Formula I, e.g., wherein the composition is substantially free of any other diastereomeric and enantiomeric form of Formula I.

1.10 Any of Composition 1 or 1.1-1.9, wherein the composition comprises less than 10% w/w (weight/weight) of any other stereoisomeric form of Formula I, e.g., less than 5% w/w of any other stereoisomeric form of Formula I, e.g., less than 4% w/w of any other stereoisomeric form of Formula I, e.g., less than 3% w/w of any other stereoisomeric form of Formula I, e.g., less than 2% w/w of any other stereoisomeric form of Formula I, e.g., less than 1% w/w of any other stereoisomeric form of Formula I.

1.11 Any of Composition 1 or 1.1-1.10, wherein the composition comprises less than 10% w/w of any other diastereomeric form of Formula I, e.g., less than 5% w/w of any other diastereomeric form of Formula I, e.g., less than 4% w/w of any other diastereomeric form of Formula I, e.g., less than 3% w/w of any other diastereomeric form of Formula I, e.g., less than 2% w/w of any other diastereomeric form of Formula I, e.g., less than 1% w/w of any other diastereomeric form of Formula I.

1.12 Any of Composition 1 or 1.1-1.11, wherein the composition comprises less than 10% w/w of any other enantiomeric form of Formula I, e.g., less than 5% w/w of any other enantiomeric form of Formula I, e.g., less than 4% w/w of any other enantiomeric form of Formula I, e.g., less than 3% w/w of any other enantiomeric form of Formula I, e.g., less than 2% w/w of any other enantiomeric form of Formula I, e.g., less than 1% w/w of any other enantiomeric form of Formula I.

1.13 Any of Composition 1 or 1.1-1.12, wherein the compound has the stereochemical configuration as shown in Formula I.

1.14 Any of Composition 1 or 1.1-1.13, wherein the composition comprises 1-60 mg of the compound of Formula I. For instance, any of Composition 1 or 1.1-1.13, wherein the composition comprises 1-10 mg, e.g., 1-9 mg (e.g., 1-8 mg) of the compound of Formula I. For instance, any of Composition 1 or 1.1-1.13, wherein the composition comprises 3 mg or 10 mg of the compound of Formula I. For instance, any of Composition 1 or 1.1-1.13, wherein the composition comprises 1 mg to less than 3 mg (e.g., 2 mg) of the compound of Formula I.

1.15 Any of Composition 1 or 1.1-1.14, wherein the composition is for once, twice, or three times daily dosing. For instance, any of Composition 1 or 1.1-1.14, wherein the composition is for once daily dosing.

Further provided are methods of prophylaxis or treatment of a central nervous system disorder (e.g., a brain disorder), for instance, a central nervous system disorder (e.g., a brain disorder) that benefits from modulating dopamine, in a patient in need thereof, wherein the method comprises administering to the patient a compound of Formula I, in free or pharmaceutically acceptable salt form (e.g., any of Formula I or 1.1-1.13 vide supra), or a pharmaceutical composition comprising a compound of Formula I, in free or pharmaceutically acceptable salt form (e.g., Formula 1.13 or any of Composition 1 or 1.1-1.15 vide supra), or a compound of Formula Ia or Compound A, in free or pharmaceutically acceptable salt form (vide infra), or a pharmaceutical composition comprising a compound of Formula Ia or Compound A, in free or pharmaceutically acceptable salt form (vide infra). Further provided are methods of prophylaxis or treatment of a central nervous system disorder (e.g., a brain disorder) that benefits from D2 receptor antagonism, D3 receptor antagonism, and/or D4 receptor antagonism in a patient in need thereof, wherein the method comprises administering to the patient a compound of Formula I, in free or pharmaceutically acceptable salt form (e.g., any of Formula I or 1.1-1.13 vide supra), or a pharmaceutical composition comprising a compound of Formula I, in free or pharmaceutically acceptable salt form (e.g., Formula 1.13 or any of Composition 1 or 1.1-1.15 vide supra), or a compound of Formula Ia or Compound A, in free or pharmaceutically acceptable salt form (vide infra), or a pharmaceutical composition comprising a compound of Formula Ia or Compound A, in free or pharmaceutically acceptable salt form (vide infra). For instance, provided are methods as described below.

Provided is a method (Method 1) for treatment or prophylaxis of a disorder (e.g., a brain disorder) in a patient in need thereof, wherein the method comprises administering to the patient an effective amount of a compound of Formula Ia:

Formula Ia

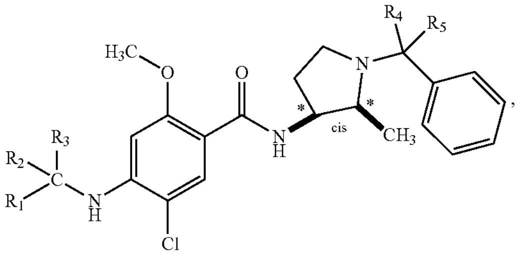

wherein:

the compound of Formula Ia has cis stereochemistry at the two stereocenters marked with asterisks in the drawing, $R_1$, $R_2$, $R_3$, $R_4$, and $R_5$ are independently selected from H and D;

in free or pharmaceutically acceptable salt form.

Further provided is Method 1 as follows:

1.1 Method 1, wherein the method comprises administering (±)-cis-N-(1-Benzyl-2-methylpyrrolidin-3-yl)-5-chloro-2-methoxy-4-methylaminobenzamide (i.e., nemonapride), in free or pharmaceutically acceptable salt form, wherein (±)-cis-N-(1-Benzyl-2-methylpyrrolidin-3-yl)-5-chloro-2-methoxy-4-methylaminobenzamide does not show optical rotation in chloroform. For instance, wherein the method comprises administering (±)-cis-N-(1-Benzyl-2-methylpyrrolidin-3-yl)-5-chloro-2-methoxy-4-methylaminobenzamide (i.e., nemonapride), in free form, wherein (±)-cis-N-(1-Benzyl-2-methylpyrrolidin-3-yl)-5-chloro-2-methoxy-4-methylaminobenzamide does not show optical rotation in chloroform.

1.2 Method 1, wherein the method comprises administering an effective amount of Compound A:

Compound A

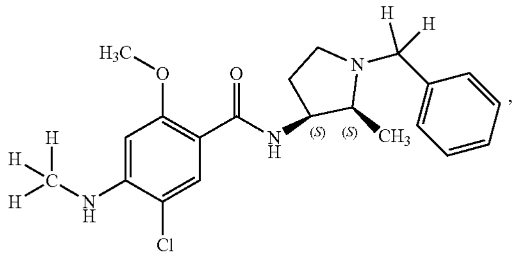

in free or pharmaceutically acceptable salt form. For instance, wherein the effective amount of Compound A, in free or pharmaceutically acceptable salt form, has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the effective amount of Compound A, in free or pharmaceutically acceptable salt form, is substantially diastereomerically and/or enantiomerically pure, e.g., wherein the effective amount of Compound A, in free or pharmaceutically acceptable salt form, is substantially diastereomerically and enantiomerically pure. For instance, wherein the effective amount of compound A, in free or pharmaceutically acceptable salt form, has a diastereomeric and/or enantiomeric excess of greater than 90%, e.g., a diastereomeric and/or enantiomeric excess equal to or greater than 95%, e.g., a diastereomeric and/or enantiomeric excess equal to or greater than 96%, e.g., a diastereomeric and/or enantiomeric excess equal to or greater than 97%, e.g., a diastereomeric and/or enantiomeric excess equal to or greater than 98%, e.g., a diastereomeric and/or enantiomeric excess equal to or greater than 99%. For instance, wherein the effective amount of compound A, in free or pharmaceutically acceptable salt form, has a diastereomeric and enantiomeric excess of greater than 90%, e.g., a diastereomeric and enantiomeric excess equal to or greater than 95%, e.g., a diastereomeric and enantiomeric excess equal to or greater than 96%, e.g., a diastereomeric and enantiomeric excess equal to or greater than 97%, e.g., a diastereomeric and enantiomeric excess equal to or greater than 98%, e.g., a diastereomeric and enantiomeric excess equal to or greater than 99%.

1.3 Method 1, wherein the method comprises administering a compound of Formula I:

Formula I

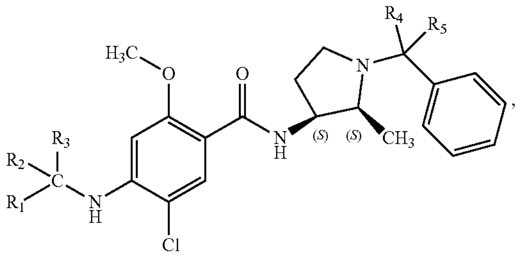

wherein:

$R_1$, $R_2$, $R_3$, $R_4$, and $R_5$ are independently selected from H and D; and at least one of $R_1$, $R_2$, and $R_3$ is D;

in free or pharmaceutically acceptable salt form.

1.4 Method 1.3, wherein $R_1$, $R_2$, $R_3$, $R_4$, and $R_5$ are D.

1.5 Method 1.3 or 1.4, wherein the method comprises administering to the patient a compound of Formula I, in free or pharmaceutically acceptable salt form, as described in any of Formula I or 1.1-1.13 vide supra. For instance, Method 1.3 or 1.4, wherein the method comprises administering to the patient a pharmaceutical composition comprising a compound of Formula I, in free or pharmaceutically acceptable salt form, as described in any of Composition I or 1.1-1.15 vide supra.

1.6 Any of Method 1.3-1.5, wherein the effective amount of the compound of Formula I, in free or pharmaceutically acceptable salt form, has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the effective amount of the compound of Formula I, in free or pharmaceutically acceptable salt form, is substantially diastereomerically and/or enantiomerically pure, e.g., wherein the effective amount of the compound of Formula I, in free or pharmaceutically acceptable salt form, is substantially diastereomerically and enantiomerically pure. For instance, wherein the effective amount of the compound of Formula I, in free or pharmaceutically acceptable salt form, has a diastereomeric and/or enantiomeric excess of greater than 90%, e.g., a diastereomeric and/or enantiomeric excess equal to or greater than 95%, a diastereomeric and/or enantiomeric excess equal to or greater than 96%, a diastereomeric and/or enantiomeric excess equal to or greater than 97%, e.g., a diastereomeric and/or enantiomeric excess equal to or greater than 98%, e.g., a diastereomeric and/or enantiomeric excess equal to or greater than 99%. For instance, wherein the effective amount of the compound of Formula I, in free or pharmaceutically acceptable salt form, has a diastereomeric and enantiomeric excess of greater than 90%, e.g., a diastereomeric and enantiomeric excess equal to or greater than 95%, e.g., a diastereomeric and enantiomeric excess equal to or greater than 96%, e.g., a diastereomeric and enantiomeric excess equal to or greater than 97%, e.g., a diastereomeric and enantiomeric excess equal to or greater than 98%, e.g., a diastereomeric and enantiomeric excess equal to or greater than 99%.

1.7 Any of Method 1 or 1.1-1.6, wherein the compound is in free form.

1.8 Method 1.3, wherein the method comprises administering an effective amount of Compound B:

Compound B

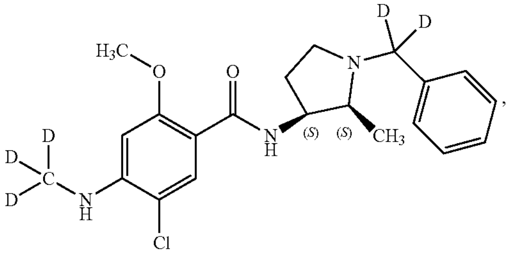

in free or pharmaceutically acceptable salt form, e.g., in free form.

1.9 Method 1.8, wherein the effective amount of Compound B, in free or pharmaceutically acceptable salt form, has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the effective amount of Compound B, in free or pharmaceutically acceptable salt form, is substantially diastereomerically and/or enantiomerically pure, e.g., wherein the effective amount of Compound B, in free or pharmaceutically acceptable salt form, is substantially diastereomerically and enantiomerically pure. For instance, wherein the effective amount of compound B, in free or pharmaceutically acceptable salt form, has a diastereomeric and/or enantiomeric excess of greater than 90%, e.g., a diastereomeric and/or enantiomeric excess equal to or greater than 95%, e.g., a diastereomeric and/or enantiomeric excess equal to or greater than 96%, e.g., a diastereomeric and/or enantiomeric excess equal to or greater than 97%, e.g., a diastereomeric and/or enantiomeric excess equal to or greater than 98%, e.g., a diastereomeric and/or enantiomeric excess equal to or greater than 99%. For instance, wherein the effective amount of compound B, in free or pharmaceutically acceptable salt form, has a diastereomeric and enantiomeric excess of greater than 90%, e.g., a diastereomeric and enantiomeric excess equal to or greater than 95%, e.g., a diastereomeric and enantiomeric excess equal to or greater than 96%, e.g., a diastereomeric and enantiomeric excess equal to or greater than 97%, e.g., a diastereomeric and enantiomeric excess equal to or greater than 98%, e.g., a diastereomeric and enantiomeric excess equal to or greater than 99%.

1.10 Any of Method 1 or 1.3-1.9, wherein the designation of deuterium (i.e., D) at a position means that position has a significantly greater than natural abundance of deuterium at that position (e.g., greater than 0.1%, or greater than 0.5%, or greater than 1%, or greater than 5%). Any atom not designated as a particular isotope is present at natural isotopic abundance.

1.11 Any of Method 1 or 1.3-1.10, wherein the compound, in free or pharmaceutically acceptable salt form, has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Method 1 or 1.3-1.10, wherein the compound, in free or pharmaceutically acceptable salt form, has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%.

1.12 Any of Method 1 or 1.1-1.11, wherein the disorder is a brain disorder. For instance, any of Method 1 or 1.1-1.11, wherein the disorder is a neuropsychiatric condition in which anhedonia is prominent.

1.13 Any of Method 1 or 1.1-1.12, wherein the disorder is an affective (mood) disorder or an anxiety disorder.

1.14 Any of Method 1 or 1.1-1.13, wherein the disorder is depression (e.g., depression associated with anhedonia), an anxiety disorder, psychosis (e.g., psychosis in neurodegenerative conditions, such as psychosis in Alzheimer's disease, Parkinson's disease, or dementia (e.g., dementia-related psychosis)), schizophrenia, schizoaffective disorder, post-traumatic stress disorder (PTSD), attention-deficit/hyperactivity disorder (ADHD), Tourette syndrome, anorexia nervosa, bulimia nervosa, binge-eating disorder, body dysmorphic disorder, obsessive compulsive disorder, addiction, bipolar disorder (including bipolar depression, bipolar mania, and bipolar disorder with mixed features), or a migraine. For instance, any of Method 1 or 1.1-1.13, wherein the anxiety disorder is panic disorder, social anxiety disorder, a phobia, or generalized anxiety disorder. Or, any of Method 1 or 1.1-1.13, wherein the method is prophylaxis or treatment of behavioral and psychological symptoms of dementia including agitation, depression, anxiety, apathy, and/or psychosis.

1.15 Any of Method 1 or 1.1-1.14, wherein the disorder is anhedonia or depression associated with anhedonia, suicidal ideation, anxious depression, inflammatory depression, treatment-resistant depression, dysthymia, bipolar depression, psychotic depression, or post-psychotic depression. For instance, any of Method 1 or 1.1-1.14, wherein the disorder is depression associated with anhedonia. Or, for instance, wherein the disorder is anhedonia. Or, for instance, any of Method 1 or 1.1-1.14, wherein the disorder is melancholic depression.

1.16 Any of Method 1 or 1.1-1.15, wherein the disorder is major depressive disorder.

1.17 Any of Method 1 or 1.1-1.14, wherein the disorder is a substance use disorder.

1.18 Any of Method 1 or 1.1-1.14, wherein the method is prophylaxis or treatment of negative symptoms of schizophrenia. Or, any of Method 1 or 1.1-1.14, wherein the method is improving cognition in schizophrenia.

1.19 Any of Method 1 or 1.1-1.11, wherein the compound, in free or pharmaceutically acceptable salt form, is administered as an anti-emetic.

1.20 Any of Method 1 or 1.1-1.19, wherein the method comprises administering 9-60 mg a day of the compound, in free or pharmaceutically acceptable salt form (i.e., 9-60 mg total daily dose of the compound, in free or pharmaceutically acceptable salt form). For instance, any of Method 1 or 1.1-1.19, wherein the method comprises administering 9-36 mg a day of the compound, in free or pharmaceutically acceptable salt form (i.e., 9-36 mg total daily dose of the compound, in free or pharmaceutically acceptable salt form).

1.21 Any of Method 1 or 1.1-1.20, wherein the method comprises administering an amount of the compound, in free or pharmaceutically acceptable salt form, that provides 55%-80% D2/D3 receptor occupancy, e.g., as measured by positron emission tomography. For instance, wherein the method comprises administering an amount of the compound, in free or pharmaceutically acceptable salt form, that provides about 65% D2/D3 receptor occupancy, e.g., as measured by positron emission tomography. Or, for instance, wherein the method comprises administering an amount of the compound, in free or pharmaceutically acceptable salt form, that provides about 60% D2/D3 receptor occupancy, e.g., as measured by positron emission tomography.

1.22 Method 1.20 or 1.21, wherein the disorder is psychosis (e.g., psychosis in neurodegenerative conditions, such as Alzheimer's disease, Parkinson's disease, and dementia (e.g., dementia-related psychosis)), schizophrenia, schizoaffective disorder, or bipolar disorder (e.g., bipolar mania).

1.23 Method 1.20 or 1.21, wherein the method is prophylaxis or treatment of negative symptoms of schizophrenia. Or, Method 1.20 or 1.21, wherein the method is improving cognition in schizophrenia.

1.24 Any of Method 1 or 1.1-1.19, wherein the method comprises administering 1-9 mg (e.g., 1-8 mg, e.g., 1.5-6 mg) a day of the compound, in free or pharmaceutically acceptable salt form (i.e., 1-9 mg total daily dose, e.g., 1-8 mg total daily dose, e.g., 1.5-6 mg total daily dose, of the compound, in free or pharmaceutically acceptable salt form). For instance, any of Method 1 or 1.1-1.19, wherein the method comprises administering 1-8 mg a day of the compound, in free or pharmaceutically acceptable salt form (i.e., 1-8 mg total daily dose of the compound, in free or pharmaceutically acceptable salt form). For instance, any of Method 1 or 1.1-1.19, wherein the method comprises administering 1-3 mg a day of the compound, in free or pharmaceutically acceptable salt form (i.e., 1-3 mg total daily dose of the compound, in free or pharmaceutically acceptable salt form). For instance, any of Method 1 or 1.1-1.19, wherein the method comprises administering 1 mg to less than 3 mg a day (e.g., 2 mg a day) of the compound, in free or pharmaceutically acceptable salt form (i.e., 1 mg to less than 3 mg total daily dose of the compound, in free or pharmaceutically acceptable salt form).

1.25 Any of Method 1, 1.1-1.19, or 1.24, wherein the method comprises administering an amount of the compound, in free or pharmaceutically acceptable salt form, that provides 10%-60% (e.g., 40%-60% or, e.g., 10%-55%, e.g., 10%-50%, e.g., 30%-50% or, e.g., 15%-50%, e.g., 15%-45%, e.g., 20%-40%, e.g., 10%-30%) D2/D3 receptor occupancy, e.g., as measured by positron emission tomography. Or, for instance, any of Method 1, 1.1-1.19, or 1.24, wherein the method comprises administering an amount of the compound, in free or pharmaceutically acceptable salt form, that provides ≤40% (e.g., about 40%), e.g., <40%, D2/D3 receptor occupancy, e.g., as measured by positron emission tomography.

1.26 Method 1.24 or 1.25, wherein the disorder is depression (e.g., depression associated with anhedonia), an anxiety disorder, post-traumatic stress disorder (PTSD), attention-deficit/hyperactivity disorder (ADHD), Tourette syndrome, anorexia nervosa, bulimia nervosa, binge-eating disorder, body dysmorphic disorder, obsessive compulsive disorder, addiction, bipolar disorder, bipolar disorder with mixed features, or a migraine. For instance, Method 1.24 or 1.25, wherein the anxiety disorder is panic disorder, social anxiety disorder, a phobia, or generalized anxiety disorder.

1.27 Any of Method 1.24-1.26, wherein the disorder is anhedonia or depression associated with anhedonia, suicidal ideation, anxious depression, inflammatory depression, treatment-resistant depression, dysthymia, bipolar depression, psychotic depression, or post-psychotic depression. For instance, wherein the disorder is anhedonia or depression associated with anhedonia.

1.28 Any of Method 1.24-1.27, wherein the disorder is major depressive disorder.

1.29 Method 1.24 or 1.25, wherein the disorder is a substance use disorder.

1.30 Any of Method 1 or 1.1-1.29, wherein the method comprises administering a pharmaceutical composition comprising the compound, in free or pharmaceutically acceptable salt form. For instance, any of Method 1 or 1.1-1.29, wherein the method comprises administering Formula 1.13 or any of Composition 1 or 1.1-1.15 vide supra.

1.31 Any of Method 1 or 1.1-1.30, wherein the method comprises administering the compound of Formula Ia, in free or pharmaceutically acceptable salt form, once, twice, or three times a day, e.g., once a day. For instance, any of Method 1 or 1.1-1.30, wherein the method comprises administering a pharmaceutical composition comprising the compound of Formula Ia, in free or pharmaceutically acceptable salt form, once, twice, or three times a day, e.g., once a day.

1.32 Any of Method 1 or 1.1-1.31, wherein the method comprises administering the compound of Formula I, in free or pharmaceutically acceptable salt form, once, twice, or three times a day, e.g., once a day. For instance, any of Method 1 or 1.1-1.31, wherein the method comprises administering a pharmaceutical composition comprising the compound of Formula I, in free or pharmaceutically acceptable salt form, once, twice, or three times a day, e.g., once a day.

1.33 Any of Method 1 or 1.1-1.32, wherein the method comprises administering Compound B, in free or pharmaceutically acceptable salt form, once, twice, or three times a day, e.g., once a day. For instance, any of Method 1 or 1.1-1.32, wherein the method comprises administering a pharmaceutical composition comprising Compound B, in free or pharmaceutically acceptable salt form, once, twice, or three times a day, e.g., once a day.

Further provided is a compound of Formula I (e.g., any of Formula 1.1-1.13) or a pharmaceutical composition disclosed herein (e.g., Formula 1.13 or any of Composition 1 or 1.1-1.15) for use in any of Method 1 or 1.1-1.33 vide supra.

Further provided is use of a compound of Formula I (e.g., any of Formula 1.1-1.13) or a pharmaceutical composition disclosed herein (e.g., Formula 1.13 or any of Composition 1 or 1.1-1.15) in any of Method 1 or 1.1-1.33 vide supra.

Further provided is use of a compound of Formula I (e.g., any of Formula 1.1-1.13) in the manufacture of a medicament (e.g., Formula 1.13 or any of Composition 1 or 1.1-1.15) for use in any of Method 1 or 1.1-1.33 vide supra.

Further provided are intermediate compounds of Formula II and Formula III, each in free or salt (e.g., pharmaceutically acceptable salt) form.

For instance, further provided is a compound of Formula II:

Formula II

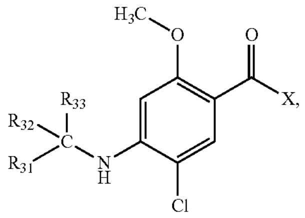

wherein $R_{31}$, $R_{32}$, and $R_{33}$ are independently selected from H and D;

X is OH or a leaving group; and at least one of $R_{31}$, $R_{32}$, and $R_{33}$ are D;

in free or salt (e.g., pharmaceutically acceptable salt) form.

Further provided are compounds of Formula II as follows:

2.1 Formula II, wherein the compound is in pharmaceutically acceptable salt form.

2.2 Formula II or 2.1, wherein $R_{31}$, $R_{32}$, and $R_{33}$ are D.

2.3 Any of Formula II, 2.1, or 2.2, wherein X is OH.

2.4 Any of Formula II, 2.1, or 2.2, wherein X is a leaving group (e.g., an activated ester, e.g., an O-acylisourea, or a halide). For instance, any of Formula II, 2.1, or 2.2, wherein the compound of Formula II is reacted with 1-ethyl-3-(3-dimethylaminopropyl)carbodiimide.

2.5 Any of Formula II or 2.1-2.3, wherein the compound is:

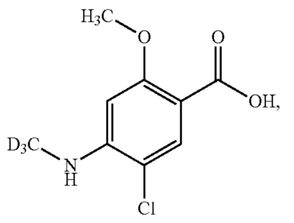 [SMILES: [2H]C([2H])([2H])Nc1cc(OC)c(C(=O)O)cc1Cl]

in free or salt (e.g., pharmaceutically acceptable salt) form, e.g., in free form.

Also further provided is a compound of Formula III:

Formula III

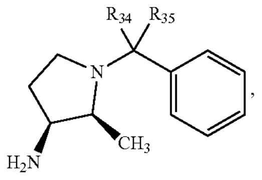

wherein:

$R_{34}$ and $R_{35}$ are D;

in free or salt (e.g., pharmaceutically acceptable salt) form.

Further provided are compounds of Formula III as follows:

3.1 Formula III, wherein the compound is in pharmaceutically acceptable salt form.

3.2 Formula III or 3.1, wherein the compound is:

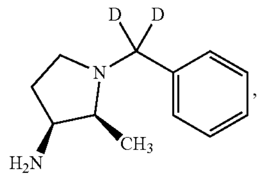 [SMILES: [2H]C([2H])(c1ccccc1)N1CC[C@H](N)[C@@H]1C]

in free or salt (e.g., pharmaceutically acceptable salt) form, e.g., in free form.

Further provided is a process (Process 1) for synthesizing a compound of Formula I (e.g., any of Formula 1.1-1.13), in free or salt (e.g., pharmaceutically acceptable salt) form.

Further provided is Process 1 as follows:

1.1 Process 1, wherein the process comprises reacting a compound of Formula II (e.g., any of Formula 2.1-2.5) with a compound of Formula III (e.g., any of Formula 3.1-3.2).

1.2 Process 1 or 1.1, wherein the process occurs in the presence of an amine (e.g., triethylamine, e.g., triethylamine and dimethylformamide).

1.3 Process 1, 1.1, or 1.2, wherein the process occurs in an organic solvent (e.g., dimethylformamide).

1.4 Any of Process 1 or 1.1-1.3, wherein the process occurs with 1-ethyl-3-(3-dimethylaminopropyl)carbodiimide and hydroxybenzotriazole. For instance, any process wherein the process occurs with 1-ethyl-3-(3-dimethylaminopropyl)carbodiimide, hydroxybenzotriazole, triethylamine, and dimethylformamide.

1.5 Any of Process 1 or 1.1-1.4, wherein the process comprises reacting a compound of Formula IIa:

Formula IIa

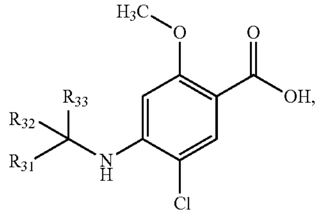

wherein $R_{31}$, $R_{32}$, and $R_{33}$ are independently selected from H and D and at least one of $R_{31}$, $R_{32}$, and $R_{33}$ is D, in free or salt (e.g., pharmaceutically acceptable salt) form, with an activating agent (e.g., 1-ethyl-3-(3-dimethylaminopropyl)carbodiimide).

1.6 Process 1.5, wherein the process forms a compound of Formula IIb:

Formula IIb

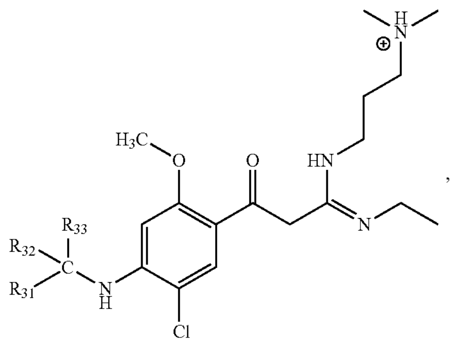

wherein $R_{31}$, $R_{32}$, and $R_{33}$ are independently selected from H and D and at least one of $R_{31}$, $R_{32}$, and $R_{33}$ is D, in free or salt (e.g., pharmaceutically acceptable salt) form.

1.7 Process 1.6, wherein the compound of Formula IIb is formed in situ.

For compounds disclosed herein, a hydrogen atom position of a structure is considered substituted with deuterium when the abundance of deuterium at that position is enriched. The natural abundance of deuterium is about 0.02%, so a compound is "enriched" with deuterium at a specific position when the frequency of incorporation of deuterium at that position exceeds 0.02%. Therefore, for deuterated compounds disclosed herein, any position designated as deuterium (i.e., D) may be enriched with deuterium at a level of greater than 0.1%, or greater than 0.5%, or greater than 1%, or greater than 5%, such as, greater than 50%, or greater than 60%, or greater than 70%, or greater than 80%, or greater than 90%, or greater than 95%, or greater than 96%, or greater than 97%, or greater than 98%, or greater than 99%. For compounds disclosed herein, any atom not designated as a particular isotope is present at natural isotopic abundance.

Compounds disclosed herein, e.g., any of Formula I (e.g., any of Formula 1.1-1.13), Formula Ia, Formula II (e.g., any of Formula 2.1-2.5), Formula III (e.g., any of Formula 3.1-3.2), Formula IIa, Formula IIb, Compound A, and Compound B, may exist in free or salt form, e.g., as acid addition salts. As used herein, unless otherwise indicated, language such as "compound of formula" is to be understood as embracing the compound in any form, for example free or acid addition salt form, or where the compound contains an acidic substituent, in base addition salt form. Compounds of Formula I (e.g., any of Formula 1.1-1.13), Formula Ia, Compound A, and Compound B are intended for use as pharmaceuticals, therefore pharmaceutically acceptable salts are preferred. Salts which are unsuitable for pharmaceutical uses may be useful, for example, for the isolation or purification of free compounds of Formula I or Formula Ia or their pharmaceutically acceptable salts, so therefore are also included.

Isolation or purification of the stereoisomers of compounds disclosed herein, for instance, Formula I (e.g., any of Formula 1.1-1.13), Formula Ia, Formula II (e.g., any of Formula 2.1-2.5), Formula III (e.g., any of 3.1-3.2), Formula IIa, Formula IIb, Compound A, and Compound B, any in free or pharmaceutically acceptable salt form, may be achieved by conventional methods known in the art, e.g., column purification, preparative thin layer chromatography, preparative HPLC, trituration, simulated moving beds, and the like.

Pure stereoisomeric forms of the compounds and intermediates disclosed herein are isomers substantially free of other enantiomeric and diastereomeric forms of the same basic molecular structure of said compounds or intermediates. "Substantially stereoisomerically pure" includes compounds or intermediates having a stereoisomeric excess of greater than 90% (i.e., more than 90% of one isomer and less than 10% of any other possible isomer). The terms "substantially diastereomerically pure" and "substantially enantiomerically pure" should be understood in a similar way, but then having regard to the diastereomeric excess and enantiomeric excess, respectively, of the material in question.

Compounds disclosed herein, e.g., any of Formula I (e.g., any of Formula 1.1-1.13), Formula Ia, Formula II (e.g., any of Formula 2.1-2.5), Formula III (e.g., any of 3.1-3.2), Formula IIa, Formula IIb, Compound A, and Compound B, any in free or pharmaceutically acceptable salt form, may be made by using the methods as described and exemplified herein and by methods similar thereto and by methods known in the chemical art. Such methods include, but are not limited to, those described below. If not commercially available, starting materials for these processes may be made by procedures, which are selected from the chemical art using techniques that are similar to or analogous to the synthesis of known compounds.

Pharmaceutically acceptable salts of any of Formula I (e.g., any of Formula 1.1-1.13), Formula Ia, Formula II (e.g., any of Formula 2.1-2.5), Formula III (e.g., any of 3.1-3.2), Formula IIa, Formula IIb, Compound A, and Compound B, may be synthesized from the parent compound which contains a basic or acidic moiety by conventional chemical methods. Generally, such salts can be prepared by reacting the free base forms of these compounds with a stoichiometric amount of the appropriate acid in an appropriate solvent.

For methods of treatment, the word "effective amount" is intended to encompass a therapeutically effective amount to treat a specific disease or disorder.

Dosages employed in practicing the present invention will of course vary depending, e.g. on the particular disease or condition to be treated, the particular compound used, the mode of administration, and the therapy desired.

Compounds disclosed herein, e.g., any of Formula I (e.g., any of Formula 1.1-1.13), Formula Ia, Compound A, or Compound B, any in free or pharmaceutically acceptable salt form, may be administered by any suitable route, including orally, parenterally, or transdermally, but are preferably administered orally.

Pharmaceutical compositions comprising compounds disclosed herein, e.g., any of Formula I (e.g., any of Formula 1.1-1.13 or any of Composition 1 or 1.1-1.15), Formula Ia, Compound A, or Compound B, any in free or pharmaceutically acceptable salt form, may be prepared using conventional diluents or excipients and techniques known in the galenic art. Thus oral dosage forms may include tablets, capsules, solutions, suspensions, and the like.

EXAMPLES

Abbreviations

AcOH=acetic acid
Boc=tert-butyloxycarbonyl
DIAD=diisopropyl azodicarboxylate
DCM=dichloromethane
DMAP=4-dimethylaminopyridine
DMF=dimethylformamide
EDCI=1-ethyl-3-(3-dimethylaminopropyl)carbodiimide
EtOAc or EA=ethyl acetate
h=hour(s)
HOBt=hydroxybenzotriazole
MeOH=methanol
MsCl=methanesulfonyl chloride
rt (or RT)=room temperature
TEA=triethylamine
TFA=trifluoroacetic acid
THF=tetrahydrofuran

Example 1

Synthesis of A1: 5-Chloro-N-((2S,3S)-1-(dideutero(phenyl)methyl)-2-methylpyrrolidin-3-yl)-2-methoxy-4-(trideuteromethylamino)benzamide

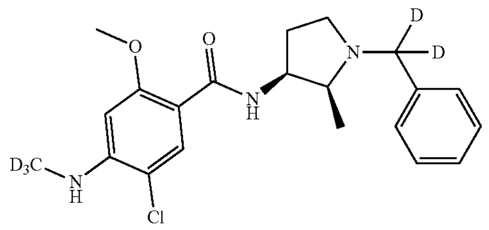 [SMILES: [2H]C([2H])([2H])Nc1cc(OC)c(C(=O)N[C@H]2CCN(C([2H])([2H])c3ccccc3)[C@H]2C)cc1Cl]

Compound 1: tert-butyl (S)-2-methyl-3,5-dioxopyrrolidine-1-carboxylate

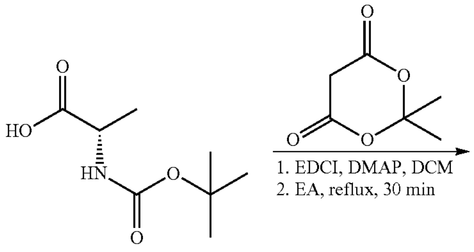

-continued

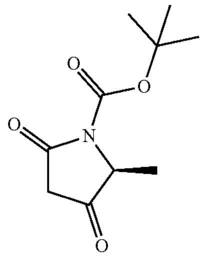

1

To a stirred solution of Boc-L-alanine (25 g, 132.1 mmol), Meldrum's acid (20 g, 138.7 mmol), and DMAP (19.4 g, 158.6 mmol) in $CH_2Cl_2$ (250 mL) is added EDCI (30.4 g, 158.6 mmol) under nitrogen at 0° C. The resulting solution is then allowed to warm up to room temperature (rt) and stirred over 16 h. It is quenched with water (50 mL), the organic phase is washed with a cold solution of 5% $KHSO_4$ (300 mLx2), water (300 mLx1) and brine, then dried over anhydrous $MgSO_4$, and concentrated to give the residue (40 g). EtOAc (200 mL) is added and the reaction mixture is refluxed for 30 minutes. The solution is concentrated and the residue is stirred in EtOAc (90 mL) at −10° C. for 2 h, then filtered, and the filter cake is collected to give the title compound as a pale yellow solid (16 g, 46% yield). $^1H$ NMR (400 MHz, $CDCl_3$) δ 4.41 (q, J=6.8 Hz, 1H), 3.22 (s, 2H), 1.57 (s, 9H), 1.51 (d, J=6.8 Hz, 3H). MS m/z (ESI): 158 $[M+H-56]^+$ Compound 2: tert-butyl (2S,3S)-3-hydroxy-2-methyl-5-oxo-pyrrolidine-1-carboxylate

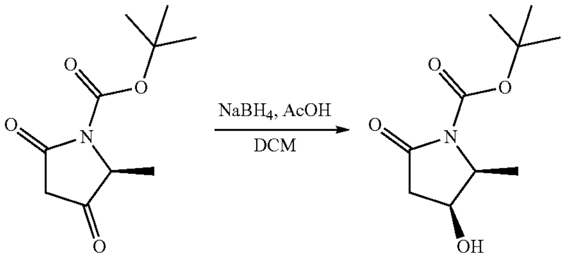

1 2

To a stirred solution of compound 1 (13 g, 61 mmol) in dichloromethane (DCM) (130 ml) is added AcOH (65 mL) at 0° C. Then $NaBH_4$ (5.77 g, 152.4 mmol) is added in three portions. The resulting solution is then allowed to warm up to room temperature and stirred over 16 h. The reaction mixture is quenched with 5% $NaHCO_3$ at 0° C. It is then extracted with DCM (200 mLx3). The combined organic layers are washed with 5% $NaHCO_3$, brine, dried over anhydrous $MgSO_4$, and concentrated to give the residue which is stirred in isopropyl ether to afford the title compound 2 (8 g, 61% yield). $^1H$ NMR (400 MHz, $CDCl_3$) δ 4.53-4.47 (m, 1H), 4.29-4.22 (m, 1H), 2.75-2.55 (m, 2H), 1.53 (s, 9H), 1.31 (d, J=6.8 Hz, 3H). MS m/z (ESI): 160 $[M+H-56]^+$ Compound 3: tert-butyl (2S,3S)-3-hydroxy-2-methyl-pyrrolidine-1-carboxylate

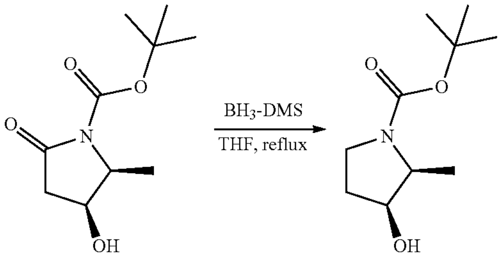

2 3

To a solution of compound 2 (3 g, 14 mmol) in dry THF (40 mL) is added a solution of $BH_3$—$SMe_2$ (21 ml, 41.8 mmol) at 0° C. and it is stirred for 30 minutes at 0° C. Then the mixture is refluxed for 4 h. The resulting mixture is cooled and quenched with saturated $NH_4Cl$ at 0° C. It is then extracted with EtOAc (100 mlx3). The organic phases are dried over anhydrous $MgSO_4$ and concentrated to give compound 3 (2.24 g, 80% yield). $^1H$ NMR (400 MHz, $CDCl_3$) δ 4.34-4.29 (m, 1H), 3.90-3.83 (m, 1H), 3.46-3.33 (m, 2H), 2.09-1.80 (m, 2H), 1.46 (s, 9H), 1.18 (d, J=6.8 Hz, 3H). MS m/z (ESI): 146 $[M+H-56]^+$ Compound 4: tert-butyl (2S,3R)-2-methyl-3-((4-nitrobenzoyl)oxy)pyrrolidine-1-carboxylate

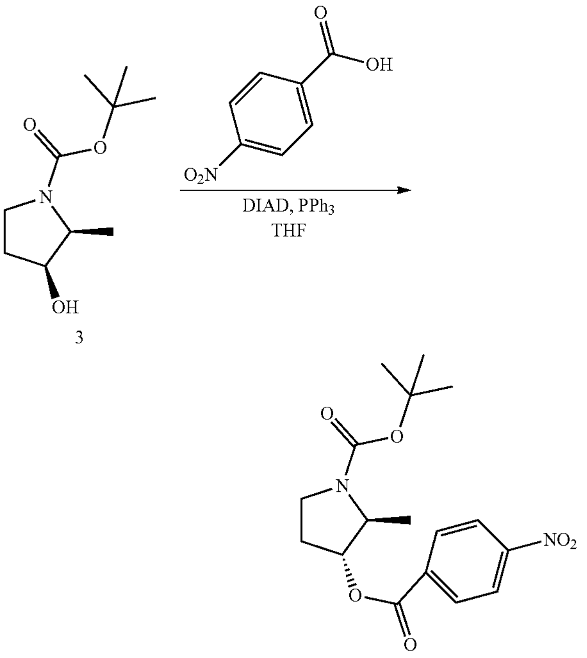

3

4

To a cold solution of compound 3 (12 g, 59.6 mmol), 4-nitrobenzoic acid (10.46 g, 62.6 mmol), and $PPh_3$ (16.42 g, 62.6 mmol) in dry THF (200 ml) is added diisopropyl azodicarboxylate (DIAD) (12.66 g, 62.6 mmol) for 30 minutes at 0° C. The reaction mixture is allowed to warm room temperature for 16 h. The resulting mixture is cooled and quenched with water. The mixture is extracted with EtOAc (200 ml×3), dried over anhydrous $MgSO_4$. It is then concentrated and purified by silica gel chromatography to afford the title compound 4 (17.1 g, 81.9% yield). $^1$H NMR (400 MHz, $CDCl_3$) δ 8.31-8.17 (m, 4H), 5.20 (d, J=4 Hz 1H), 4.17-3.86 (m, 1H), 3.59-3.46 (m, 2H), 2.35-2.11 (m, 2H), 1.48 (s, 9H), 1.28 (d, J=6.8 Hz, 3H). MS m/z (ESI): 295 $[M+H-56]^+$ Compound 5: (2S,3R)-2-methylpyrrolidin-3-yl 4-nitrobenzoate

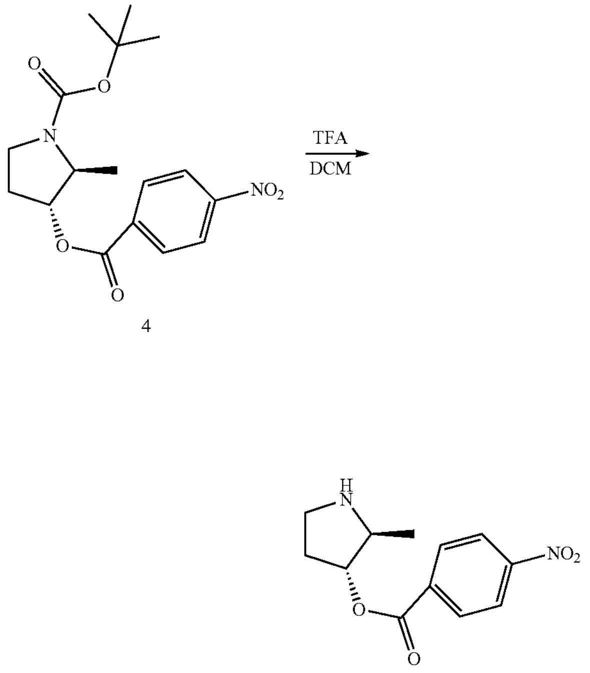

4

5

A mixture of compound 4 (16.1 g, 46 mmol) and trifluoroacetic acid (TFA) (80 mL) in DCM (160 mL) is stirred at room temperature for 1 h. The reaction mixture is then concentrated to give the product 5 (11.5 g, 100% yield). MS m/z (ESI): 251 $[M+H]^+$ Compound 6: (2S,3R)-1-benzoyl-2-methylpyrrolidin-3-yl 4-nitrobenzoate

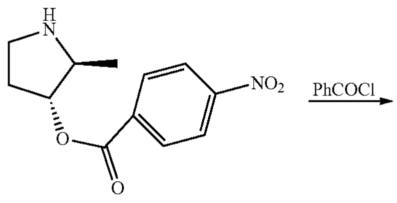

5

-continued

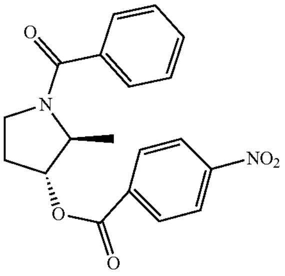

6

To a solution of compound 5 (11.5 g, 46 mmol) in toluene (360 ml) is added 2N NaOH (360 ml, 72 mmol), then benzoyl chloride (6.6 g, 46 mmol) in toluene (150 ml) is added at 0° C. The mixture is separated and the aqueous phase is extracted with DCM (250 ml×3). The organic phase is dried over $MgSO_4$ and concentrated to give compound 6 (14.0 g, 85.9% yield). MS m/z (ESI): 355 $[M+H]^+$ Compound 7: ((2S,3R)-3-hydroxy-2-methylpyrrolidin-1-yl)(phenyl)methanone

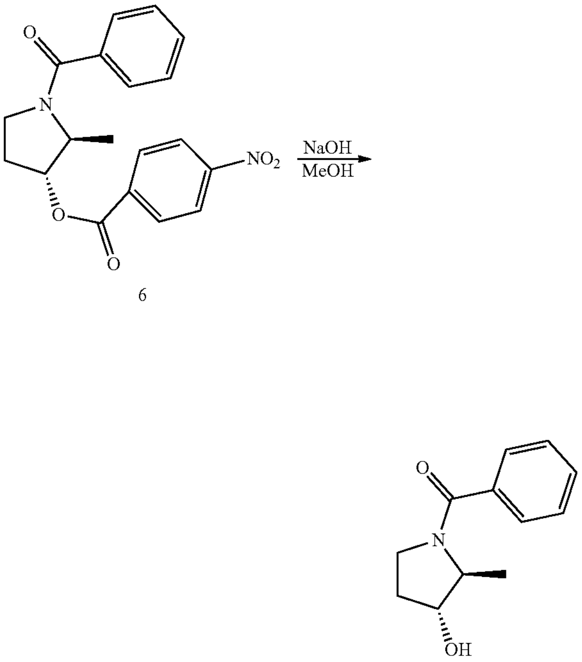

6

7

To a stirred solution of compound 6 (14 g, 39.5 mmol) in MeOH (350 mL) is added 6N NaOH (6.6 ml, 39.6 mmol). The reaction mixture is stirred for 40 minutes and then concentrated under reduced pressure. The residue is diluted with DCM (200 ml) and water (100 ml), the aqueous phase is extracted with DCM (250 ml×3). The organic phase is dried over $MgSO_4$ and concentrated to give the residue which is treated with petroleum ether (PE) (9 ml) and EtOAc (3 ml) to afford the title compound 7 (7.1 g, 87.6% yield). MS m/z (ESI): 206 $[M+H]^+$

Compound 8: (2S,3R)-1-(dideutero(phenyl)methyl)-2-methylpyrrolidin-3-ol

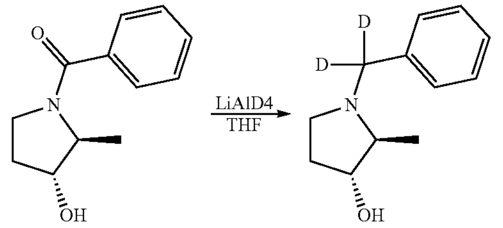

7 8

To a stirred solution of compound 7 (1.6 g, 7.8 mmol) in dry THF (30 mL) is slowly added lithium aluminum deuteride (372 mg, 7.8 mmol) in portions at −15° C. The reaction mixture is stirred to room temperature for 18 hours. The mixture is cooled to 0° C. and quenched with 20% aqueous KOH (2 mL). The mixture is filtered and washed with diethyl ether. The combined organic phases are dried over $Na_2SO_4$ and concentrated to give the residue that is purified by silica gel chromatography to afford the title compound 8 (1.5 g, 99% yield). MS m/z (ESI): 194 $[M+H]^+$

Compound 9: (2S,3S)-3-azido-1-(dideutero(phenyl)methyl)-2-methylpyrrolidine

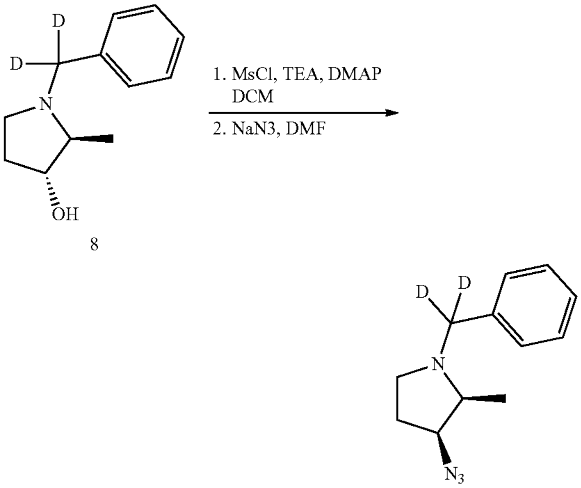

8

9

To a stirred solution of compound 8 (1.5 g, 7.8 mmol), DMAP (2.36 g, 0.78 mmol), and $Et_3N$ (95 mg, 23.4 mmol) in dry $CH_2Cl_2$ at 0° C. is added MsCl (1.8 g, 15.62 mmol). The reaction mixture is stirred for 3 hours at room temperature, then quenched with saturated aqueous $NaHCO_3$, and the aqueous layer extracted with $CHCl_3$ (30 mL×3). The combined organic phases are washed with brine and dried over anhydrous $Na_2SO_4$. The organic phase is concentrated under reduced pressure and the residue is diluted with DMF (40 ml) and $NaN_3$ (1.65 g, 23.4 mmol) is added. The reaction mixture is stirred for 16 h at 80° C. It is quenched with water, extracted with EtOAc (100 ml×3). The organic phases are dried over $MgSO_4$ and concentrated to give the residue which is purified by silica gel column chromatography to afford the title compound 9 (1.64 g, 96% yield). MS m/z (ESI): 219 $[M+H]^+$ LCMS: M+1=219

Compound 10: (2S,3S)-1-(dideutero(phenyl)methyl)-2-methylpyrrolidin-3-amine

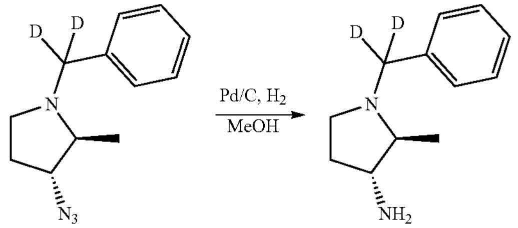

9 10

A mixture of compound 9 (1.64 g, 3 mmol) and 10% of Pd/C (182 mg) in MeOH (50 mL) is stirred under $H_2$ for 18 hours. The reaction mixture is filtered and the solvent evaporated under reduced pressure to afford the title compound 10 (1 g, 66% yield). MS m/z (ESI): 193 $[M+H-56]^+$

Compound 11: Methyl 4-(tert-butoxycarbonylamino)-5-chloro-2-methoxybenzoate

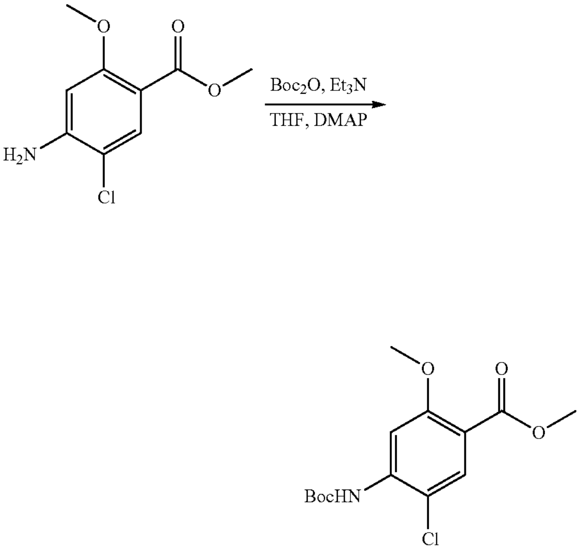

11

To a mixture of methyl 4-amino-5-chloro-2-methoxybenzoate (5 g, 23.2 mmol), DMAP (1.4 g, 11.7 mmol), and triethylamine (13.2 mL) in THF (175 mL) is added $Boc_2O$ (5.6 g, 25.5 mmol) and the reaction mixture is stirred at 38° C. for 6 h. It is concentrated to give the residue that is purified by silica gel column chromatography to afford the compound 11 (4.4 g, 60% yield). $^1H$ NMR (400 MHz, $CDCl_3$) δ 8.71 (s, 1H), 7.72 (s, 1H), 7.62 (s, 1H), 3.81 (s, 3H), 3.77 (s, 3H), 1.49 (s, 9H). MS m/z (ESI): 316 $[M+H-56]^+$ Compound 12: Methyl 4-(tert-butoxycarbonyl(trideuteromethyl)amino)-5-chloro-2-methoxybenzoate

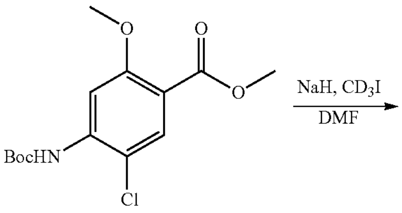

11

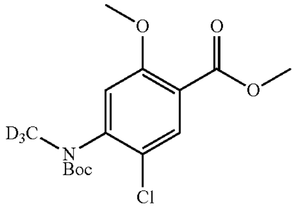

12

To a solution of compound 11 (1.96 g, 6.2 mmol) in dry DMF (40 mL) is added NaH (370 mg, 9.3 mmol) and the reaction is stirred at room temperature for 30 minutes, then $CD_3I$ (1.8 g, 12.4 mmol) is added and the reaction is stirred at room temperature for 3 h. The reaction is cooled to 0° C. and quenched with saturated aqueous $NH_4Cl$. It is extracted with EtOAc (100 mL) and the organic phase is washed with water, brine, and dried over anhydrous $Na_2SO_4$. The organic phase is concentrated under reduced pressure and the residue purified by silica gel column chromatography to afford the title compound 12 (2.02 g, 97.6% yield). NMR (400 MHz, $CDCl_3$) δ 7.86 (s, 1H), 6.85 (s, 1H), 3.90 (s, 6H), 1.36 (s, 9H). MS m/z (ESI): 277 $[M+H-56]^+$ Compound 13: 4-(tert-Butoxycarbonyl(trideuteromethyl)amino)-5-chloro-2-methoxybenzoic acid

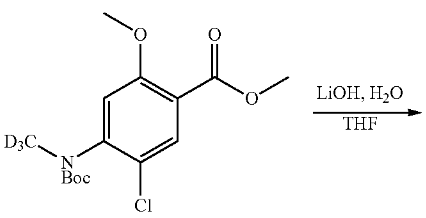

12

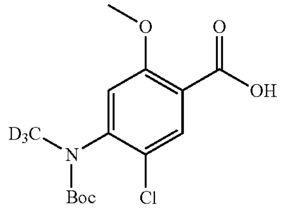

13

To a solution of compound 12 (1.68 g, 5.1 mmol) in THF (65 mL) and water (20 mL) is added $LiOH{\cdot}H_2O$ (844 mg, 20 mmol) and the mixture is stirred for 12 h. The reaction is acidified to pH=3 with 1N HCl and then is extracted with EtOAc (50 mL×3) and the combined organic phases are washed with brine and dried over anhydrous $Na_2SO_4$. The organic phase is concentrated under reduced pressure and the residue is purified by silica gel column chromatography to afford the title compound 13. (1.46 g, 90% yield). $^1H$ NMR (400 MHz, $CDCl_3$) δ 8.23 (s, 1H), 6.96 (s, 1H), 4.08 (s, 3H), 1.39 (s, 9H). MS m/z (ESI): 263 $[M+H-56]^+$ Compound 14: 5-Chloro-2-methoxy-4-(trideuteromethylamino)benzoic acid

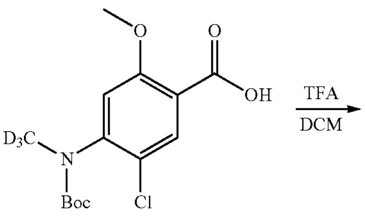

13

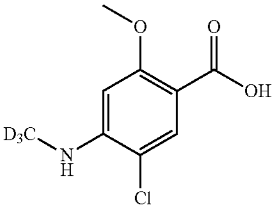

14

A mixture of compound 13 (1.44 g, 4.5 mmol) and TFA (12 mL) in $CH_2Cl_2$ (25 mL) is stirred at room temperature for 1 h. The reaction mixture is concentrated to give compound 14 (0.73 g, 73.8% yield). $^1H$ NMR (400 MHz, DMSO-d6) δ 7.61 (s, 1H), 6.20 (s, 1H), 6.18 (s, 1H), 3.83 (s, 3H). MS m/z (ESI): 219 $[M+H]^+$ A1: 5-Chloro-N-((2S,3S)-1-(dideutero(phenyl)methyl)-2-methylpyrrolidin-3-yl)-2-methoxy-4-(trideuteromethylamino)benzamide

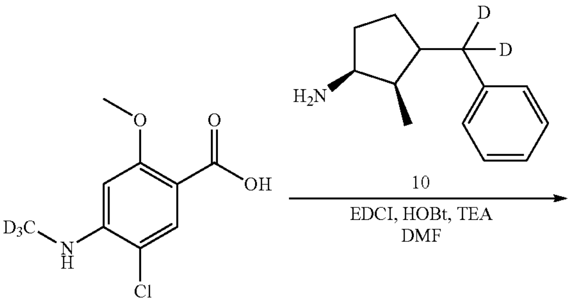

14

-continued

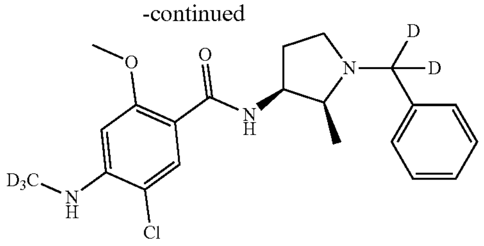

A1

A mixture of compound 10 (100 mg, 0.52 mmol), compound 14 (114 mg, 0.52 mmol), HOBt (105 mg, 0.78 mmol), EDCI (150 mg, 0.78 mmol), and TEA (158 mg, 1.56 mmol) in dry DMF (2 ml) is stirred at room temperature for 16 h. The resulting mixture is quenched with water and extracted with EtOAc (15 mL×3), washed with brine, dried over anhydrous $MgSO_4$, and concentrated to give the residue which is purified by silica gel chromatography to afford the title compound A1 (87 mg, 42.3% yield). $^1H$ NMR (400 MHz, $CDCl_3$) δ 8.10 (s, 1H), 7.99 (s, 1H), 7.52-7.35 (m, 5H), 6.13 (s, 1H), 4.69 (s, 2H), 4.00 (s, 3H), 2.97 (s, 1H), 2.63 (s, 1H), 2.21-2.05 (m, 2H), 1.59 (s, 1H), 1.13 (s, 3H). MS m/z (ESI): 393 [M+H]+

Example 2—Radioligand Binding Competition Activity on Recombinant Human Dopamine and Serotonin Receptors Using Filtration Binding Assays Radioligand binding experiments are conducted with membrane preparations. Receptor accession numbers, cellular background, and reference compounds are listed in Table 1.

TABLE 1

| Receptor | Accession Number | Cell Line | Reference Tracer | Reference Competitor |
|---|---|---|---|---|
| D2S | NP_057658.2 | CHO-K1 | [$^3$H]-Spiperone | Risperidone |
| D3 | AAA73929.1 | CHO-K1 | [$^3$H]-R-(+)-7-OH-DPAT | R-(+)-7-OH-DPAT |
| D4.4 | NP_000788.2 | CHO-K1 | [$^3$H]-Spiperone | Haloperidol |
| 5-HT1A | NP_000515.2 | CHO-K1 | [$^3$H]-8-OH-DPAT | 5-HT |
| 5-HT2A | NP_000612.1 | CHO-K1 | [$^3$H]-Ketanserin | Ketanserin |
| 5-HT7A | NP_000863.1 | CHO-K1 | [$^3$H]-LSD | 5-CT |
| human D2L | AAB26819.1 | CHO-K1 | [$^3$H]-Spiperone | Risperidone |

The compound from Example 1 (A1) is tested for radioligand binding competition activity at human Dopamine D2S, D2L, D3, and D4.4 and Serotonin 5-HT1A, 5-HT2A, and 5-HT7A receptors and results are provided in Table 2.

TABLE 2

| | Binding | | | | | | |
|---|---|---|---|---|---|---|---|
| Measure | D2S | D3 | D4 | 5-HT1A | 5-HT2A | 5-HT7A | D2L |
| Nemonapride[a] ($IC_{50}$, nM) | 0.5 | 0.3 | 0.8 | 2.7 | 10 | 75.7 | 0.95 |
| Nemonapride[a] (Ki, nM) | 0.1 | 0.2 | 0.4 | 1.4 | 2.3 | 53.2 | 0.01 |
| cis (S,S) nemonapride[b] ($IC_{50}$, nM) | 0.5 | 0.6 | 6.5 | 53.4 | 13 | 167 | 0.09 |
| cis (S,S) nemonapride[b] (Ki, nM) | 0.1 | 0.3 | 3.2 | 26.7 | 2.9 | 117 | 0.01 |
| Ex. 1 (A1, S,S) ($IC_{50}$, nM) | 0.6[c] (0.76, 0.44) | 0.4[c] (0.37, 0.45) | 3.3[c] (5.21, 1.3) | 45.0[c] (38.1, 51.8) | 16.4[c] (16.0, 16.8) | 100[c] (94.4, 106) | 0.1 |
| Ex. 1 (A1, S,S) (Ki, nM) | 0.1 | 0.2 | 1.6 | 22.5 | 3.7 | 74.4 | 0.01 |

[a](±)-cis-N-(1-Benzyl-2-methylpyrrolidin-3-yl)-5-chloro-2-methoxy-4-methylaminobenzamide

[b]N-[(2S,3S)-1-benzyl-2-methylpyrrolidin-3-yl]-5-chloro-2-methoxy-4-(methylamino)benzamide

[c]Average of numbers in parentheses.

Example 3—Agonist or Antagonist Activity on Recombinant Human Dopamine and Serotonin Receptors Using IPOne HTRF, cAMP HTRF, and GTPyS Assays SPA $^{35}$S-GTPgS experiments are conducted with membrane preparations. IP-One and cAMP HTRF assays are conducted with recombinant cell lines. Receptor accession numbers, cellular background, and reference compounds are listed in Table 3.

TABLE 3

| Receptor | Accession Number | Assay | Cell Line | Reference Agonist | Reference Antagonist |
|---|---|---|---|---|---|
| D2S | NP_057658.2 | cAMP | CHO-K1 | Quinpirole | Haloperidol |
| D3 | AAA73929.1 | GTP | CHO-K1 | Dopamine | GR103691 |
| D4.4 | NP_000788.2 | cAMP | CHO-K1 | Dopamine | Spiperone |
| 5-HT1A | NP_000515.2 | cAMP | CHO-K1 | 5-CT | Not tested |
| 5-HT2A | NP_000612.1 | IPOne | CHO-K1 | α-Me-5-HT | Ketanserin |
| 5-HT7A | NP_000863.1 | cAMP | CHO-K1 | 5-CT | Risperidone |
| D2L | AAB26819.1 | cAMP | CHO-K1 | Quinpirole | Haloperidol |

The compound from Example 1 (A1) is tested for antagonist activity at human Dopamine D2S, D2L, D3, and D4.4 receptors, for agonist activity at human Serotonin 5-HT1A receptor, for agonist and antagonist activity at human Serotonin 5-HT2A receptor, and for antagonist activity at human Serotonin 5-HT7A receptor. Results are in Tables 4 and 5.

Agonist activity of test compounds is expressed as a percentage of the activity of the reference agonist at its $EC_{100}$ concentration. Antagonist activity of the test compound is expressed as a percentage of the inhibition of reference agonist activity at its $EC_{80}$ concentration.

TABLE 4

| Functional Assays | | | | | | | |
|---|---|---|---|---|---|---|---|
| Measure ($IC_{50}$, nM) | D2 (antagonist mode) | D3 (antagonist mode) | D4 (antagonist mode) | 5-HT1A (agonist mode) $EC_{50}$ | 5-HT2A (agonist mode) $EC_{50}$ | 5-HT2A (antagonist mode) $EC_{50}$ | 5-HT7A (antagonist mode) |
| Nemonapride[a] | cAMP 0.3 (D2S) cAMP 0.08 (D2L) | GTPγS 3.0 | cAMP 0.9 | cAMP 14.3 | IP-one 5.5 | IP-one 6.5 | — |
| cis (S,S) nemonapride[b] | cAMP 0.3 (D2S) cAMP 0.09 (D2L) | GTPγS 7.4 | cAMP 1.9 | cAMP >100 | IP-one 2.8 | IP-one 2.4 | — |
| Ex. 1 (A1) | cAMP 1.1[c] (1.93, 0.26) (D2S) cAMP 0.1 (D2L) | GTPγS 2.4[c] (2.01, 2.76) | cAMP 15.3[c] (24.1, 6.58) | cAMP >3000 | IP-one 2.5[c] (1.26, 5.20, 1.15) | IP-one 14.1[c] (24, 4.26) | cAMP 2240 |

[a]((±)-cis-N-(1-Benzyl-2-methylpyrrolidin-3-yl)-5-chloro-2-methoxy-4-methylaminobenzamide)

[b]N-[(2S,3S)-1-benzyl-2-methylpyrrolidin-3-yl]-5-chloro-2-methoxy-4-(methylamino)benzamide

[c]Average of numbers in parentheses.

TABLE 5

| Measure[a] | D2 (antagonist mode) | D3 (antagonist mode) | D4 (antagonist mode) | 5-HT1A (agonist mode) | 5-HT2A (agonist mode) | 5-HT2A (antagonist mode) | 5-HT7A (antagonist mode) |
|---|---|---|---|---|---|---|---|
| Nemonapride[b] | cAMP 97 (D2S) cAMP 86 (D2L) | GTPγS 126 | cAMP 75 | cAMP 52 | IP-one 48 | IP-one 33 | — |
| cis (S,S) nemonapride[c] | cAMP 88 (D2S) cAMP 84 (D2L) | GTPγS 117 | cAMP 67 | cAMP 17 | IP-one 29 | IP-one 52 | — |

TABLE 5-continued

| Measure[a] | D2 (antagonist mode) | D3 (antagonist mode) | D4 (antagonist mode) | 5-HT1A (agonist mode) | 5-HT2A (agonist mode) | 5-HT2A (antagonist mode) | 5-HT7A (antagonist mode) |
|---|---|---|---|---|---|---|---|
| Ex. 1 (A1) | cAMP 98[d] (104, 91) (D2S) cAMP 81 (D2L) | GTPγS 129[d] (135, 123) | cAMP 89[d] (103, 75) | cAMP 0.6 | IP-one 27[d] (43, 19, 36, 10) | IP-one 39[d] (32, 46) | — |

[a]Top % Inhibition or Activation at maximal concentration
[b]((±)-cis-N-(1-Benzyl-2-methylpyrrolidin-3-yl)-5-chloro-2-methoxy-4-methylaminobenzamide)
[c]N-[(2S,3S)-1-benzyl-2-methylpyrrolidin-3-yl]-5-chloro-2-methoxy-4-(methylamino)benzamide
[d]Average of numbers in parentheses.

As shown above, the deuterated compound of Example 1 is a D2/D3/D4 antagonist.

TABLE 6

| Functional Assays | | |
|---|---|---|
| Measure for Ex. 1 (A1) | 5-HT1A (antagonist mode) | 5-HT2B (antagonist mode) |
| $EC_{50}$ (nM) | 1900 | 3.4 |
| $E_{max}$ | 63% | 92% |

Example 4—In Vitro Metabolism

Study compounds are investigated in pooled cryopreserved human (mixed gender) hepatocytes. The incubations are performed using 5 μM initial concentration and sampling at 0, 60, and 120 minute time points. The samples are analyzed using UPLC-QE-orbitrap-MS. Incubation volume: 300 μl in 48-well plate. Number of cells: 1 million viable cells/ml. Test compound: 5 μM (stock solution in DMSO). Incubation medium: pH 7.4, Bioreclamation IVT in vitro KHB medium. Shaking: 600 rpm. Time points: 0, 60, and 120 minutes with and without cells. Temperature: 37° C. Sampling volume: 60 μl. DMSO content in incubation: 0.5%. Termination of incubations: 2-fold volume of 75% acetonitrile. Control: verapamil disappearance rate.

Sample preparation for hepatocyte samples: Samples are centrifuged for 20 min at 2272×g at room temperature and pipetted to a UPLC-plate for analysis.

Data are shown in FIG. 1 and the table below. In FIG. 1, the dashed line is without cells and the solid line is with cells.

TABLE 7

| Compound | Incubation | 0 min, % | 60 min, % | 120 min, % |
|---|---|---|---|---|
| Compound from Example 1 (A1) | Human | 100 | 10 | 3 |
| | Buffer | 100 | 88 | 80 |

Example 5—In Vivo Pharmacokinetics

Group A male Sprague-Dawley (SD) rats are dosed (by PO) with test compound at 0.5 mg/kg and 5 mg/kg (N=3 animals/dose level). Blood samples are obtained at 5, 10, and 30 minutes, and 1, 2, 4, 8, and 24 hours after dosing. Following blood collection at 24 hours, brain perfusion is performed on the animals before harvesting brain tissues.

Group B male Sprague-Dawley (SD) rats are dosed (by PO) with test compound at 0.5 mg/kg and 5 mg/kg (N=9 animals/dose level). At designated timepoints (1, 4, and 8 hours), three animals from each dose group undergo blood draw followed by brain perfusion before samples are collected.

Test compound is the deuterated compound of Example 1 (A1).

Rats are surgically cannulated with femoral artery catheter for blood collection. Approximate weight of rats is 250-350 g. Water is provided ad libitum. Fasting overnight prior to oral dose. Food available 4 h post dose.

Dose formulations are 0.5% aqueous methylcellulose (4000 cps) with 0.1% Tween™80 for PO administration. Once prepared, the suspension is vortexed/homogenized and continuously stirred until administration. Dose concentration: 0.1 mg/mL for 0.5 mg/kg dose and 1 mg/mL for 5 mg/kg dose. Route of administration: oral gavage. Dose volume: 5 mL/kg. Serial bleed: 200 μL per time point. Terminal bleed: 500 μL.

Blood samples are obtained via an automated sampling system in tubes containing potassium EDTA anticoagulant up to 24 h post dose. Plasma is obtained by centrifugation and snap frozen on dry ice within 30 minutes after collection. Aliquots of each dose formulation are taken, diluted appropriately, and analyzed at the same time with plasma samples by LC-MS/MS.

Plasma (harvested from blood samples) and brain tissues (homogenized and processed) are analyzed by LC/MS/MS. Plasma is harvested from blood via centrifugation within 30 minutes of sample collection. Brain tissue is collected after animals undergo perfusion to remove residual cardiovascular blood.

Dose solutions, plasma (harvested from blood), and brain tissues (homogenized and processed) are stored at −20° C. until analysis.

Plasma samples are thawed at room temperature before adding an organic solvent containing an internal standard to precipitate proteins.

Brain samples are thawed and homogenized in water (3-4 volumes) and aliquots of homogenates analyzed by LC/MS/MS.

Figure 2:
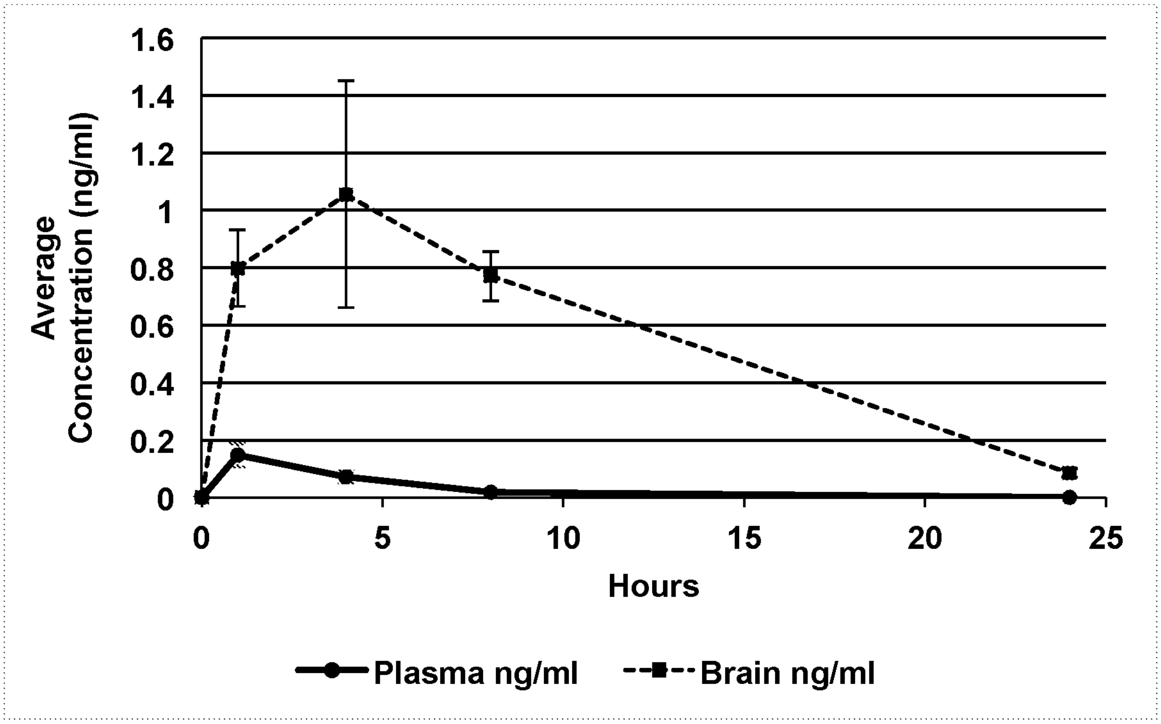
FIG. 2 shows extended brain enrichment of the compound of Example 1 (A1) in rats following a single PO dose of 0.5 mg/kg compared to plasma levels.
Figure 3:
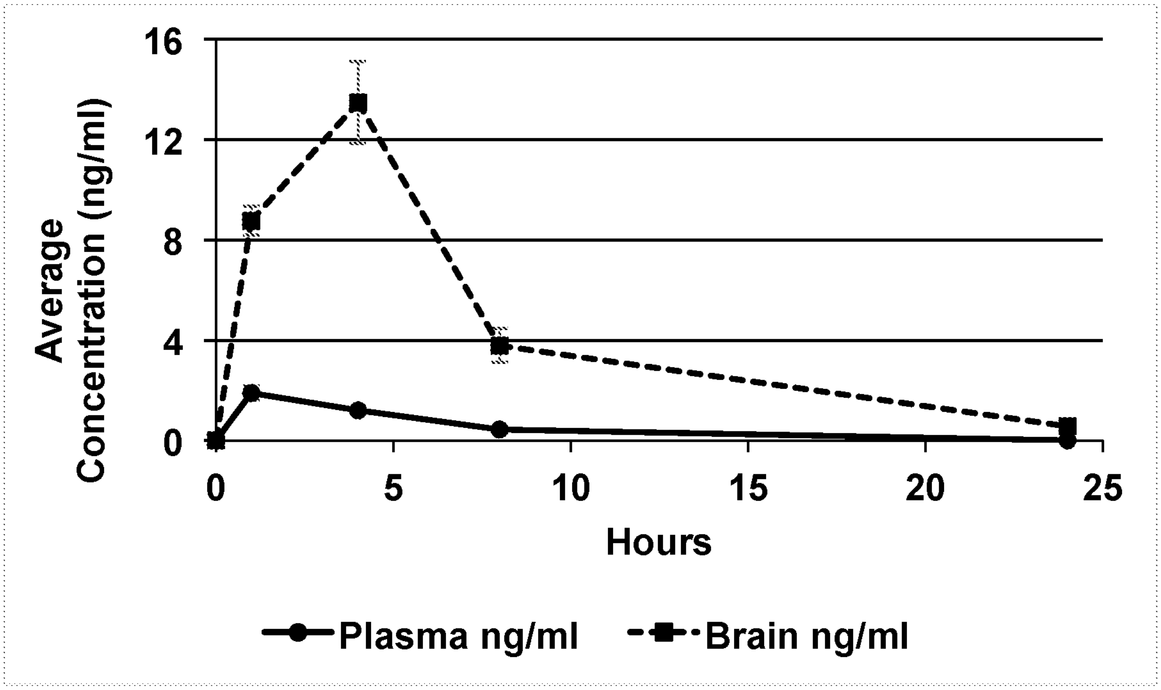
FIG. 3 shows extended brain enrichment of the compound of Example 1 (A1) in rats following a single PO dose of 5 mg/kg compared to plasma levels.

Results are shown in FIGS. 2 and 3.

The extended brain enrichment of the compound of Example 1 (A1) in rats following single PO doses of 0.5 mg/kg and 5 mg/kg compared to plasma levels is shown in FIG. 2 and FIG. 3, respectively. In each figure, average brain concentration (ng/ml) is shown as the dashed line and average plasma concentration (ng/ml) is shown as the solid line.

The plasma half-life of the compound of Example 1 (A1) at 0.5 mg/kg is about 2 hours. While plasma concentrations reduce, maximum brain concentration is reached at about 4 hours post dose.

Example 6—Ex Vivo Radioligand Binding in Membrane Preparations to Determine Time-Course of Receptor Occupancy at Central $D_2$ Receptors This study is to determine receptor occupancy at central D2 receptors following oral administration of the deuterated compound of Example 1 (A1) at various time points (1, 2, 4, 8, and 24 hours) and the positive comparator, olanzapine (10 mg/kg, po), using [$^3$H]raclopride and rat striatal membranes. Liquid scintillation counting is used to quantify radioactivity.

Animals

Thirty-five male Sprague-Dawley rats. Standard pelleted diet and filtered water is available ad libitum.

Drug Treatment

On day of test, animals are dosed orally with either vehicle, a single dose (2.5 mg/kg) of the deuterated compound of Example 1 (A1), olanzapine (10 mg/kg, po), or N-[(2S,3S)-1-benzyl-2-methylpyrrolidin-3-yl]-5-chloro-2-methoxy-4-(methylamino)benzamide (cis (S,S) nemonapride) (2.5 mg/kg). Rats are sacrificed at 1 (N=5 rats), 2 (N=5 rats), 4 (N=5 rats), 8 (N=5 rats), and 24 (N=5 rats) hours after drug administration or 1 hour after vehicle and olanzapine administration (N=5 rats for vehicle and N=5 rats for olanzapine). Vehicle is 0.5% methylcellulose.

Pharmacokinetics

A post-mortem blood sample (approx. 5 ml) is taken by cardiac puncture and placed into K/EDTA tubes. The post-mortem blood samples are gently inverted, centrifuged (1900 g for 5 minutes at 4° C.), and 1 ml of plasma from taken for PK determination. All plasma samples are frozen and stored at −80° C.

Whole brains are removed, rinsed with saline, and blot dried. The left striatum and right striatum is dissected out and weighed before being frozen on dry ice. The striata from each hemisphere are frozen separately. The tissue is wrapped in aluminum foil, placed in bags, and stored at −20° C. until the day of the assay.

[$^3$H]Raclopride Binding

Homogenate Preparation

The striata is homogenised individually in ice-cold 50 mM Tris, pH 7.4, 120 mM NaCl, 5 mM KCl, 2 mM $AlCl_2$, 1 mM $MgCl_2$, and 10 μM pargyline using a tight-fitting homogeniser equivalent to 6.25 mg wet weight of tissue/ml and used immediately in the binding assay.

Assay

Striatal homogenates (400 μl, equivalent to 2.5 mg wet weight tissue/tube) are incubated with 50 μl of 1.6 nM [$^3$H]raclopride and either 50 μl assay buffer (total binding) or 50 μl of 1 μM (−)sulpiride (to define non-specific binding) for 30 minutes at 23° C. The assay buffer consists of 50 mM Tris, pH 7.4, 120 mM NaCl, 5 mM KCl, 2 mM $CaCl_2$, 1 mM $MgCl_2$, and 10 μM pargyline. The wash buffer consists of 50 mM Tris, pH 7.4. There are two tubes for the determination of total binding and two tubes for the determination of non-specific binding.

Membrane bound radioactivity is recovered by filtration under vacuum through filters, presoaked in 0.5% polyethylenimine (PEI) using a cell harvester. Filters are rapidly washed with ice-cold buffer and radioactivity determined by liquid scintillation counting.

Data Analysis

A value for specific binding (dpm) is generated by the subtraction of mean non-specific binding (dpm) from mean total binding (dpm) for each animal.

Figure 4:
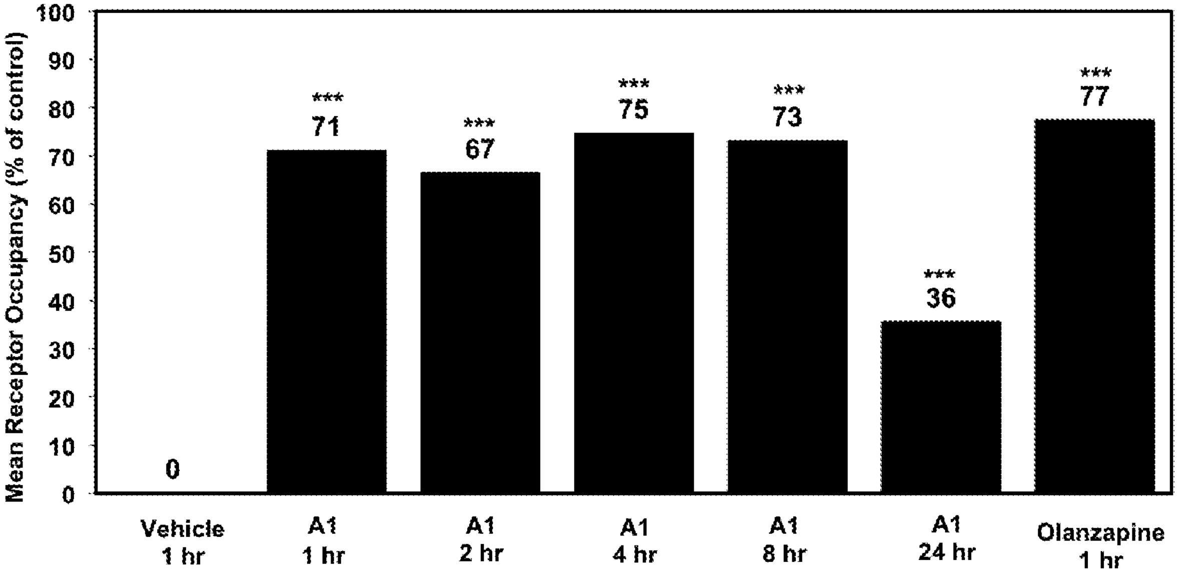
FIG. 4 shows D2 receptor occupancy of the compound of Example 1 (A1) when administered orally at a dose of 2.5 mg/kg to rats.

Results are shown in FIGS. 4, 6, 8, and 9. FIG. 4 shows D2 receptor occupancy of the compound of Example 1 (A1) when administered orally at a dose of 2.5 mg/kg to rats. Compared to FIG. 6, FIG. 4 excludes one data point at the 1 hour time point that is later determined should be included and which is included in the FIG. 6 graph.

Results in FIG. 4 are expressed as mean receptor occupancy as a percentage of control taken as 0% (n=4-5). Data is square root transformed and analyzed by one-way ANOVA with treatment as a factor. Comparisons to vehicle are by Williams' test for the deuterated compound of Example 1 (A1) and by multiple t test for olanzapine. ***p<0.001.

Figure 6:
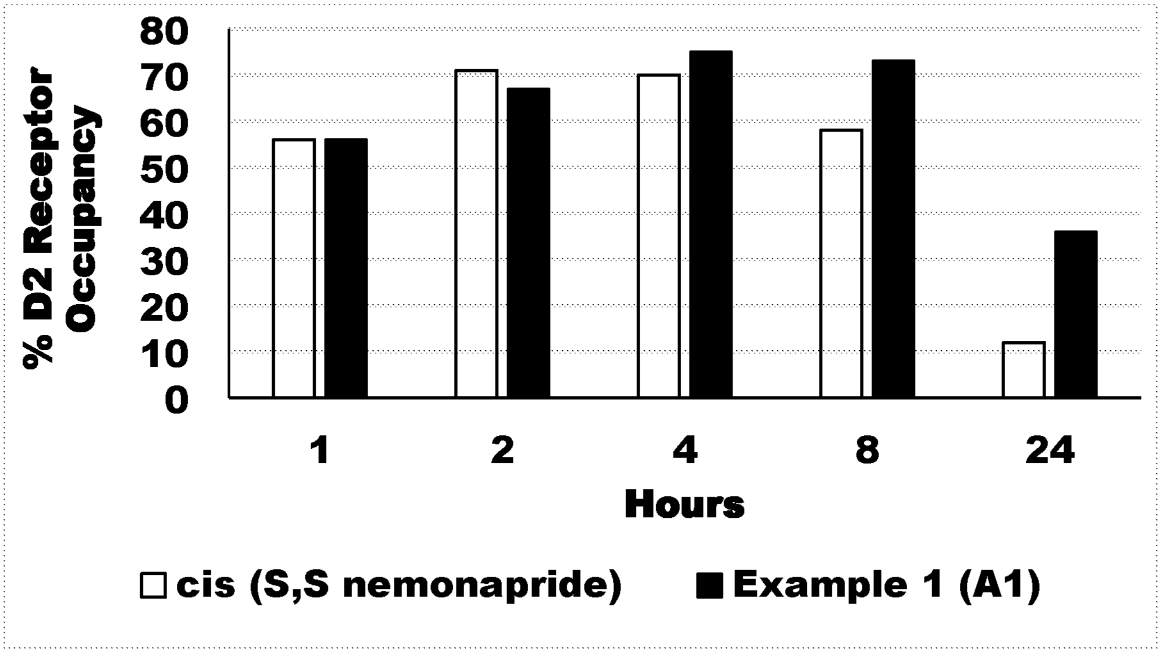
FIG. 6 shows D2 receptor occupancy of cis (S,S) nemonapride and the compound of Example 1 (A1) when administered orally at a dose of 2.5 mg/kg to rats.
Figure 7:
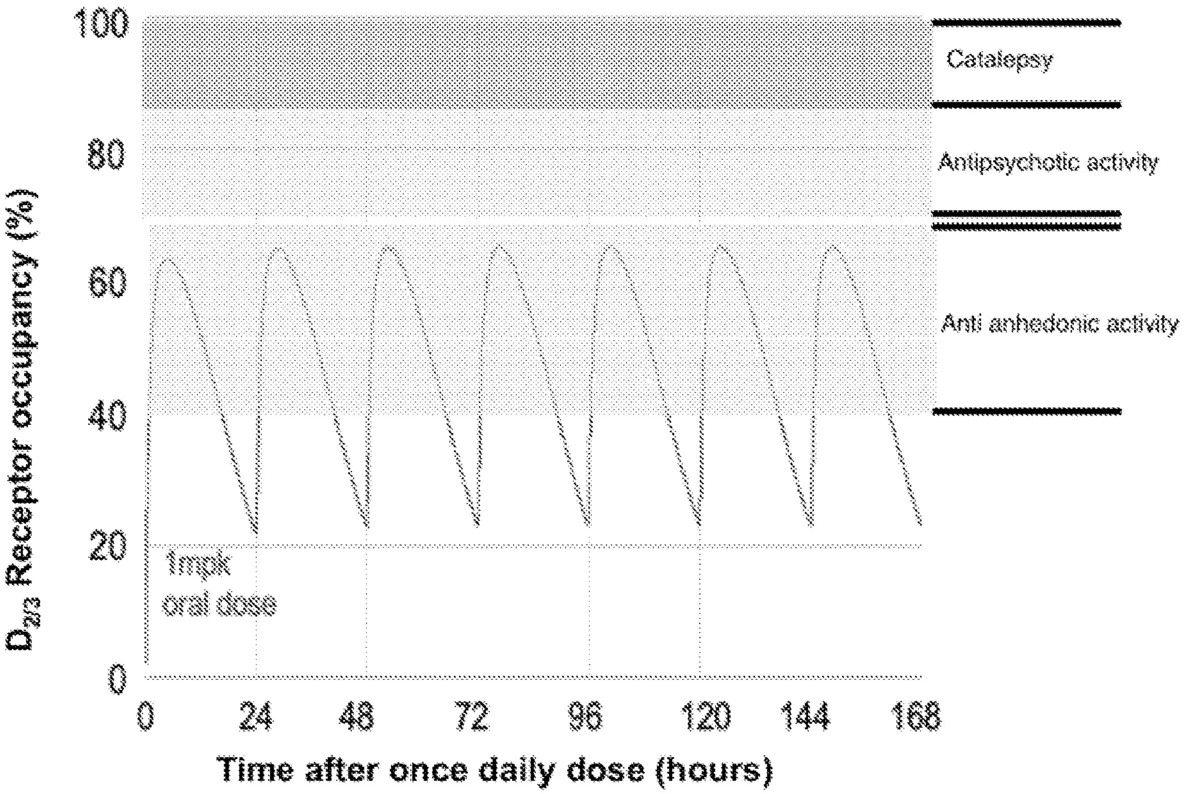
FIG. 7 shows a pharmacokinetic:pharmacodynamic model for the compound of Example 1 (A1).

FIG. 6 shows the deuterated compound of Example 1 (A1) has higher receptor occupancy levels at 4 h, 8h, and 24h compared to N-[(2S,3S)-1-benzyl-2-methylpyrrolidin-3-yl]-5-chloro-2-methoxy-4-(methylamino)benzamide (cis (S,S) nemonapride).

Figure 8:
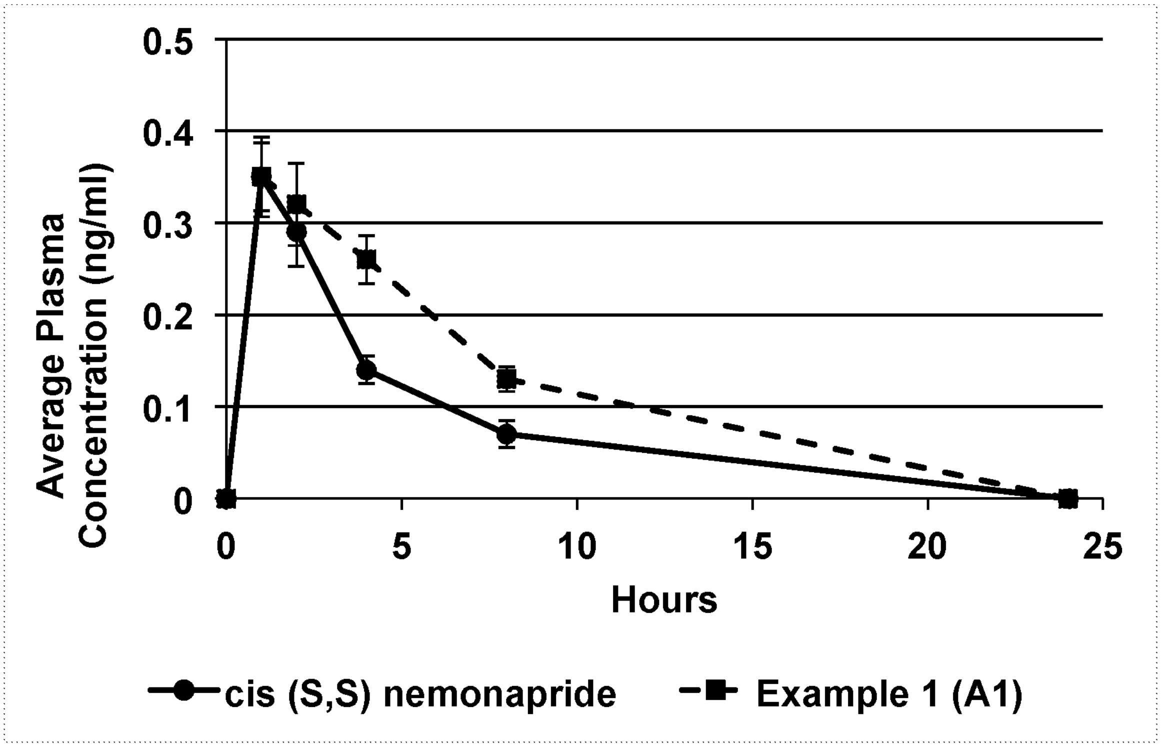
FIG. 8 shows average plasma concentration (ng/ml) in rats of cis (S,S) nemonapride and the compound of Example 1 (A1) following single oral administration of 2.5 mg/kg.

Plasma pharmacokinetics between N-[(2S,3S)-1-benzyl-2-methylpyrrolidin-3-yl]-5-chloro-2-methoxy-4-(methylamino)benzamide (cis (S,S) nemonapride) and the deuterated compound of Example 1 (A1) are shown in FIG. 8. In FIG. 8, average data for cis (S,S) nemonapride data is shown as the solid line and average data for the deuterated compound of Example 1 (A1) is shown as the dashed line (single oral administration of 2.5 mg/kg of each compound).

The brain enrichment and retention of the compound of Example 1 (A1) in rats following single oral administration of 2.5 mg/kg compared to plasma levels is seen by comparing FIG. 8 and FIG. 9.

The deuterated compound of Example 1 (A1) has enriched and retained brain levels compared to N-[(2S,3S)-1-benzyl-2-methylpyrrolidin-3-yl]-5-chloro-2-methoxy-4-(methylamino)benzamide (cis (S,S) nemonapride) (see FIG. 9) (single oral administration of 2.5 mg/kg of each compound).

In addition, as discussed above, FIG. 6 shows the deuterated compound of Example 1 (A1) has higher receptor occupancy levels at 4 h, 8h, and 24h compared to N-[(2S,3S)-1-benzyl-2-methylpyrrolidin-3-yl]-5-chloro-2-methoxy-4-(methylamino)benzamide (cis (S,S) nemonapride).

Example 7—Touchscreen-Based Rat Probabilistic Reward Task

The Probabilistic Reward Task (PRT) uses visual discrimination methodology to quantify reward responsiveness to both identify deficits and characterize drug-induced improvements. Groups of rats are trained on the touchscreen-based PRT and exposed to asymmetrical probabilistic contingencies to generate response biases to the richly rewarded stimulus (Pizzagalli, D. et al., Biological Psychiatry, 2005, 57, 319-327; Kangas, B. et al., Translational Psychiatry, 2020, 10(1):285; Wooldridge, L. et al., International Journal of Neuropsychopharmacology, 2021, 24, 409-418). Next, subjects are tested with vehicle and three doses of the deuterated compound of Example 1 (A1).

Methods

Subjects

Male Sprague Dawley rats are used in the present study.

Apparatus

Details and schematics of the rodent touch-sensitive experimental chamber can be found in Kangas, B. et al., Behavioural Pharmacology, 2017, 28, 623-629. Briefly, a custom-built Plexiglas chamber (25×30×35 cm) is situated in a sound- and light-attenuating enclosure (40×60×45 cm).

A 17" touch-sensitive screen (1739L, ELO TouchSystems, Menlo Park, CA) comprises the inside right-hand wall of the enclosure. An infusion pump (PHM-100-5, Med Associates, St. Albans, VT) outside the enclosure is used to deliver sweetened condensed milk solution into the shallow reservoir of a custom-designed aluminum receptacle. The receptacle is mounted 3 cm above the floor bars and centered on the left-hand inside wall. Both touchscreen and fluid reservoir are easily accessible to the subject. A speaker bar (NQ576AT, Hewlett-Packard, Palo Alto, CA) mounted above the touchscreen is used to emit audible feedback. All experimental events and data collection are programmed in E-Prime Professional 2.0 (Psychology Software Tools, Inc., Sharpsburg, PA).

Procedure

Initial Training

Modified response-shaping techniques are used to train rats to engage with the touchscreen (Kangas, B. et al., Journal of Neuroscience Methods, 2012, 209, 331-336). A 5×5 cm blue square on a black background is presented in different sections of the touchscreen (left, right or center), with the proviso that its lower edge always is 10 cm above the floor bars. This requires the rat to rear on its hind legs to reach the screen and make a touchscreen response with its paw. Each response is reinforced with 0.1 mL of 30% sweetened condensed milk and the delivery is paired with an 880 ms yellow screen flash and 440 Hz tone and followed by a 5-sec intertrial interval (ITI) blackout period. After responses are reliably observed with latencies <5 sec following stimulus presentation, line-length discrimination training commenced.

Line-Length Discrimination Training

Discrete trials begin with concurrent presentation of a white line presented 5 cm above left and right response boxes. The width of the line is always 7 cm, but the length of the line is either 30 cm or 15 cm and varies in a quasi-random fashion across 100-trial sessions (50 trials of each length). Subjects learn to respond to the left or right response box depending on the length of the white line (i.e., long line=respond left, short line=respond right, or vice versa). Response box designation is counter-balanced across subjects. A correct response is reinforced as described above and is followed by a 5 sec ITI, whereas an incorrect response immediately results in a 5 sec ITI. A correction procedure (Kangas, B. et al., Journal of the Experimental Analysis of Behavior, 2008, 90, 103-112) is implemented during initial discrimination training—each incorrect trial is repeated until a correct response is made—and is discontinued after session-wide trial repeats are <5 in each trial type. Discrimination sessions continue without correction until accuracies for both line lengths are >75% correct for 3 consecutive sessions.

Probabilistic Reward Task

Following line-length discrimination training, probabilistic reinforcement schedules are introduced. Based on the human task protocol, a 3:1 rich/lean probabilistic schedule is arranged such that 60% of correct responses to one of the line lengths (e.g., long line=rich alternative) and 20% of correct responses to the other line length (e.g., short line=lean alternative) are rewarded. Rich/lean line assignment is counterbalanced across subjects and 50 trials of each trial type are presented in a quasi-random sequence. These probabilistic contingencies are assessed across 5 consecutive sessions prior to initiation of drug testing.

PRT Drug Tests

Following the establishment of probabilistic contingencies, an acute drug testing protocol is arranged that includes intermittent maintenance sessions in which correct responses on all trials are reinforced, control sessions in which 3:1 (60%:20%) rich/lean probabilistic contingencies are arranged and, no more than once per week, a drug testing session in which vehicle or a dose of the deuterated compound of Example 1 (A1) (0.5, 1, or 2.5 mg/kg) is tested by administering it orally, 4-5 hr prior to a 3:1 (60%:20%) probabilistic session. Doses of the deuterated compound of Example 1 (A1) are tested in a mixed order across subjects using a Latin Square design. Vehicle and all doses of the deuterated compound of Example 1 (A1) are tested in all subjects.

Data Analysis

The implementation of probabilistic contingencies yields two primary dependent measures: response bias and task discriminability. These can be quantified by examining the number of Correct and Incorrect responses in rich and lean trial types using, respectively, log b and log d equations derived from signal detection theory (Kangas, B. et al., Journal of the Experimental Analysis of Behavior, 2008, 90, 103-112; Luc O. et al., Perspectives on Behavior Science, 2021, 44 (4), 517-540; McCarthy, D., Signal Detection: Mechanisms, Models, and Applications (eds Nevin, J. et al.), Behavioral Detection Theory: Some Implications for Applied Human Research, 1991 (Erlbaum, New Jersey)).

$$\log b = 0.5 * \log\left(\frac{(\text{Rich}_{Correct} + 0.5) * (\text{Lean}_{Incorrect} + 0.5)}{(\text{Rich}_{Incorrect} + 0.5) * (\text{Lean}_{Correct} + 0.5)}\right)$$

$$\log d = 0.5 * \log\left(\frac{(\text{Rich}_{Correct} + 0.5) * (\text{Lean}_{Correct} + 0.5)}{(\text{Rich}_{Incorrect} + 0.5) * (\text{Lean}_{Incorrect} + 0.5)}\right)$$

High bias values are produced by high numbers of correct responses during rich trials and incorrect responses during lean trials, which increase the log b numerator. High discriminability values are produced by high numbers of correct responses during both rich and lean trials, which increase the log d numerator. (0.5 is added to all parameters to avoid instances where no errors are made on a given trial type, which would make log transformation impossible.) All data (log b, log d, accuracy, reaction time) are subject to repeated measures analysis of variance (ANOVA).

Drugs

The deuterated compound of Example 1 (A1) is dissolved in a 0.5% methylcellulose solution. Drug doses are administered orally 4-5 hr prior to the experimental session.

Results and Discussion

Figure 5A:
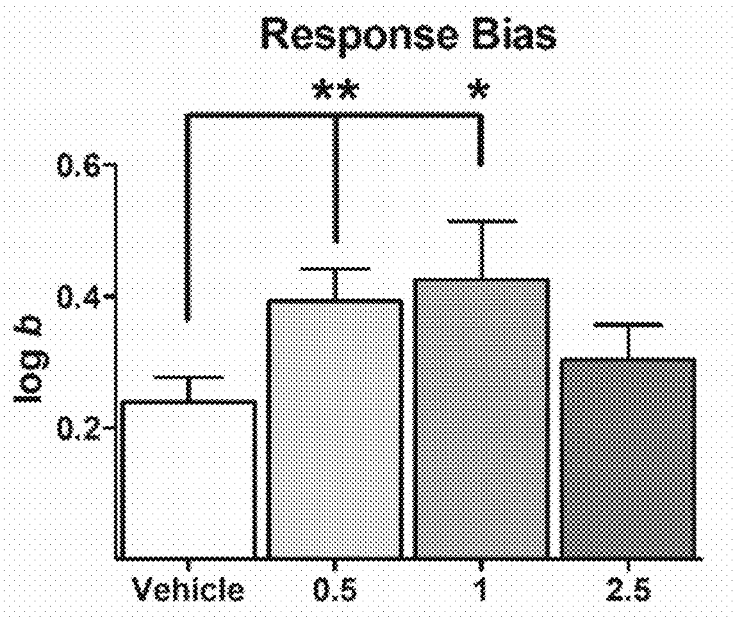
FIG. 5A shows response bias in the probabilistic reward task for the compound of Example 1 (A1) when administered at doses of 0.5, 1, and 2.5 mg/kg to rats.

As shown in FIG. 5A, there is response bias for rich stimulus specifically at doses of 0.5 and 1 mg/kg of the deuterated compound of Example 1 (A1).

As shown FIG. 5A, administration of 0.5 and 1 mg/kg of the deuterated compound of Example 1 (A1) increases the group mean log b relative to sessions following treatment with vehicle. Administration of 2.5 mg/kg also produces group average increases, but to a lesser extent.

Figure 5B:
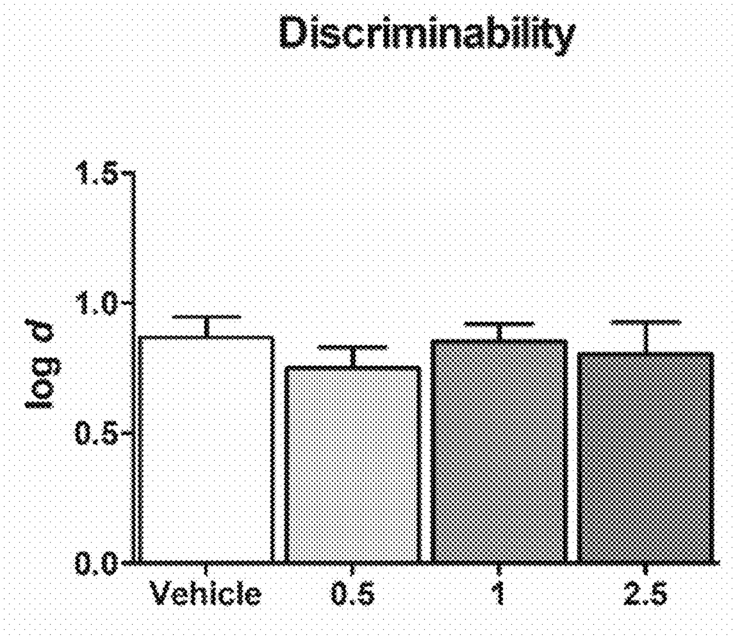
FIG. 5B shows discriminability in the probabilistic reward task for the compound of Example 1 (A1) when administered at doses of 0.5, 1, and 2.5 mg/kg to rats.

As shown in FIG. 5B, discriminability (log d) values are similar to vehicle following the doses tested. Within the context of the PRT, this comparator supports the fact that the increases in log b detailed above are not simply due to drug-induced decrements in task discriminability or overall accuracy.

The data shows that doses of the deuterated compound of Example 1 (A1) targeting low but not high $D_2$ RO significantly increase reward responsiveness. This is revealed by substantive increases in response bias (log b) without reductions in task discriminability (log d). General linear model tests of within-subjects contrast (quadratic term) yield statistical significance across the dose-response function for the deuterated compound of Example 1 (A1) ($F[1, 7]=5.69$; $p=0.048$). Paired t-test analyses of log b values confirm the statistical significance of each dose-related effect. Paired t-test analyses show that low doses are significantly different than vehicle (0.5 mg/kg: n=8, paired t-test $p=0.006$; Cohen's d=1.21 and 1 mg/kg: n=8, paired t-test $p=0.04$; Cohen's d=0.75), but not 2.5 mg/kg (n=8, paired t-test $p=0.1$; Cohen's d=0.5). Log d values are not reduced at any doses tested for the deuterated compound of Example 1 (A1).

No catalepsy is observed at tested doses.

Data shows that the deuterated compound of Example 1 (A1) may reduce anhedonia at low doses without inducing extrapyramidal side effects.

Data suggests that D2/3 receptor occupancy of about 40-60% provides antianhedonic effects, D2/3 receptor occupancy of about 65-80% provides antipsychotic effects, and catalepsy emerges above 80% receptor occupancy.

Example 8

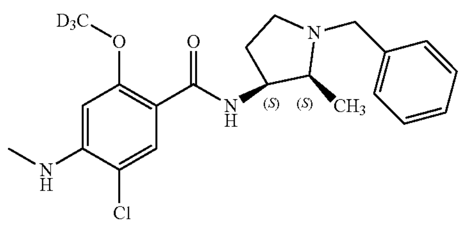

T1

Compound T1 above is synthesized similar to Example 1 with appropriate deuterated fragment. In vivo pharmacokinetics in rats for single oral doses of 0.5 mg/kg and 5 mg/kg of T1 are determined similar to Example 5.

Group A male Sprague-Dawley (SD) rats are dosed (by PO) with test compound at 0.5 mg/kg and 5 mg/kg (N=3 animals/dose level). Blood samples are obtained at 5, 10, and 30 minutes, and 1, 2, 4, 8, and 24 hours after dosing. Following blood collection at 24 hours, brain perfusion is performed on the animals before harvesting brain tissues.

Group B male Sprague-Dawley (SD) rats are dosed (by PO) with test compound at 0.5 mg/kg and 5 mg/kg (N=9 animals/dose level). At designated timepoints (1, 4, and 8 hours), three animals from each dose group undergo blood draw followed by brain perfusion before samples are collected.

Test compound is T1 above.

Dose formulation is 0.5% aqueous methylcellulose (4000 cps) with 0.1% Tween™80 for PO administration. Dose concentration: 0.1 mg/mL for 0.5 mg/kg dose and 1 mg/mL for 5 mg/kg dose. Dose volume: 5 mL/kg.

Pharmacokinetic data for the deuterated compound of Example 1 (A1) and T1 are in Tables 8 and 9 below and shown in FIGS. 10-13. Data for the deuterated compound of Example 1 (A1) is from Example 5.

TABLE 8

| Plasma | | | | |
|---|---|---|---|---|
| | Dose (mg/kg) | | | |
| | 0.5 | | 5 | |
| | Compound | | | |
| | T1 | A1 | T1 | A1 |
| Cmax (ng/mL) | 0.21 | 0.11 | 2.11 | 6.13 |
| Tmax (h) | 0.69 | 0.56 | 0.83 | 0.28 |
| AUC (ng · h/mL) | 0.58 | 0.31 | 6.62 | 9.41 |

TABLE 9

| Brain | | | | |
|---|---|---|---|---|
| | Dose (mg/kg) | | | |
| | 0.5 | | 5 | |
| | Compound | | | |
| | T1 | A1 | T1 | A1 |
| Cmax (ng/mL) | 0.77 | 1.06 | 7.99 | 13.47 |
| Tmax (h) | 4 | 4 | 1 | 4 |
| AUC (ng · h/mL) | 10.66 | 13.69 | 55.86 | 107.10 |
| Brain/Plasma Ratio | 18.50 | 44.58 | 8.44 | 11.38 |

Figure 11:
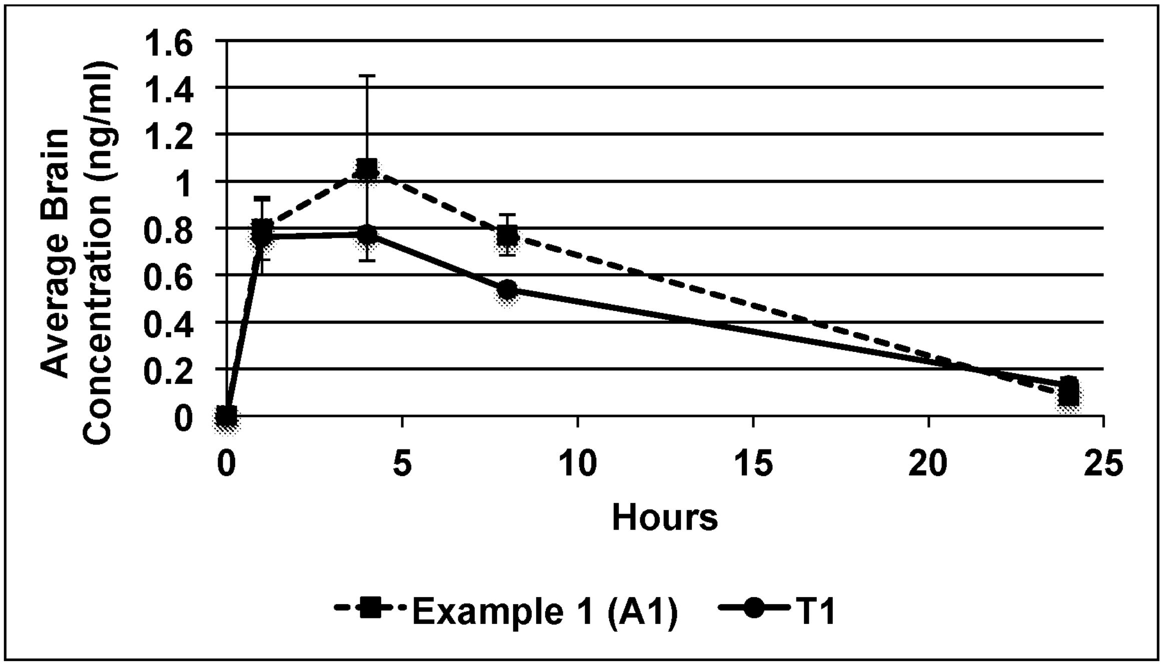
FIG. 11 shows average brain concentration (ng/ml) in rats of T1 and the compound of Example 1 (A1) following single oral administration of 0.5 mg/kg.
Figure 12:
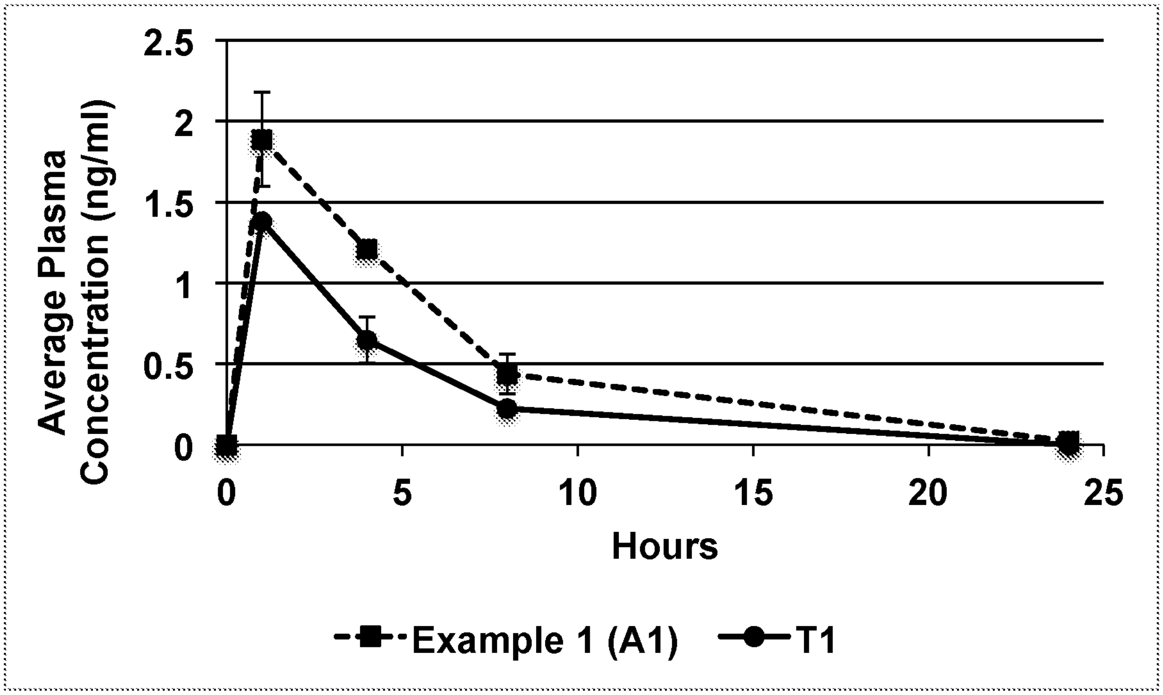
FIG. 12 shows average plasma concentration (ng/ml) in rats of T1 and the compound of Example 1 (A1) following single oral administration of 5 mg/kg.
Figure 13:
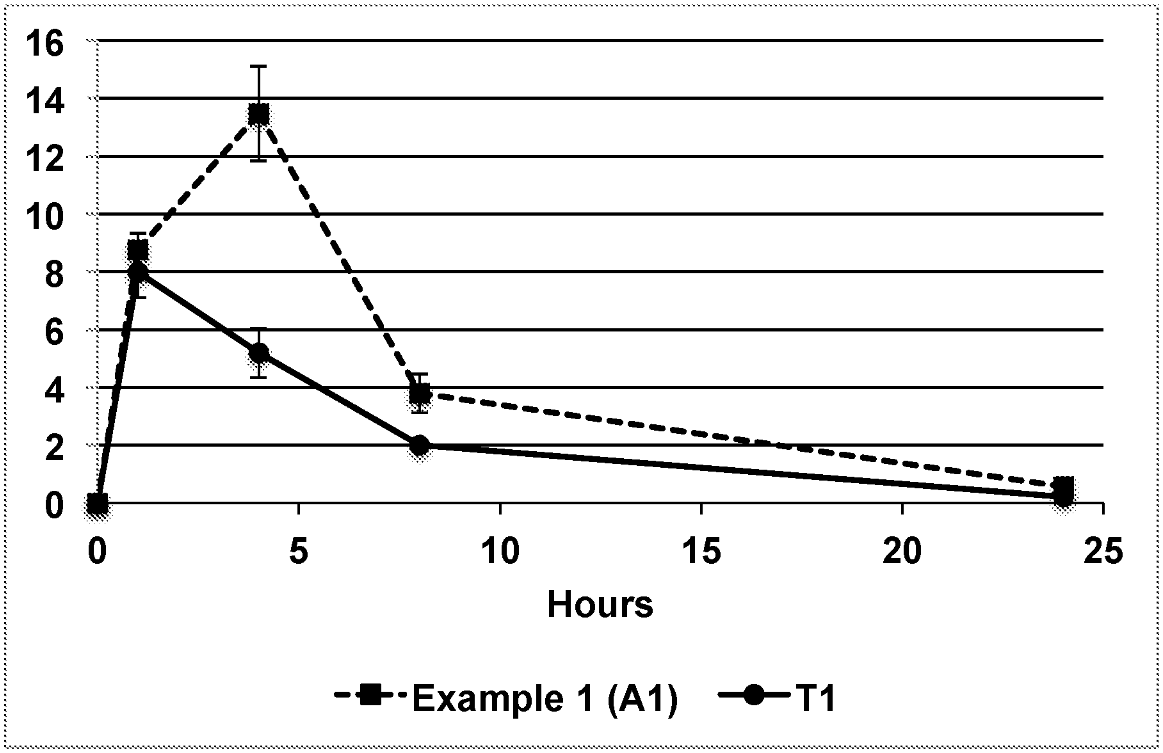
FIG. 13 shows average brain concentration (ng/ml) in rats of T1 and the compound of Example 1 (A1) following single oral administration of 5 mg/kg.

The brain AUC of the deuterated compound of Example 1 (A1) is 2-fold higher than T1 at 5 mg/kg. The deuterated compound of Example 1 (A1) has better brain/plasma ratios than T1 at both dose levels. FIG. 11 shows that at 8 hours, brain levels of the compound of Example 1 (A1) are similar to the highest levels of T1 measured, which occur at shorter time.

Example 9—Conditioned Avoidance Response

Adult male Sprague Dawley rats are used. Risperidone (0.5 mg/kg; Sigma Aldrich) is dissolved in 10% DMSO in water and injected i.p. at a dose volume of 1 mg/kg 30 minutes prior to test. The deuterated compound of Example 1 (A1) (0.5, 2.5, and 5 mg/kg) is formulated in 0.5% methyl cellulose in water and administered orally at a dose volume of 1 mg/kg 4 hours prior to test.

The Conditioned Avoidance Response (CAR) Test is an animal model screening for antipsychotic drugs.

Dunnett's post hoc analysis reveals that risperidone (0.5 mg/kg) and the deuterated compound of Example 1 (A1) (2.5 and 5 mg/kg) significantly decrease percent avoidance as well as the number of avoidance responses compared to vehicle.

Dunnett's post hoc analysis reveals that risperidone (0.5 mg/kg) and the deuterated compound of Example 1 (A1) (5 mg/kg) increase escape failures compared to vehicle.

Rats treated acutely with the deuterated compound of Example 1 (A1) (2.5 and 5 mg/kg) show decreased avoidance responses and percent avoidance indicating potential antipsychotic activity. The deuterated compound of Example 1 (A1) (5 mg/kg) shows a slight increase in escape failures.

Example 10—Headshake Response

Adult male Sprague Dawley rats are used. The deuterated compound of Example 1 (A1) (1, 5, and 10 mg/kg) is formulated in 0.5% methylcellulose solution and administered orally (PO) at a dose volume of 1 ml/kg 4 hours prior to test. DOI (3 mg/kg) is dissolved in saline and administered IP at a dose volume of 1 ml/kg (10 minutes prior to test).

Animals are administered vehicle, DOI, or test compound and returned to their holding cage for the appropriate pretreatment time (10 minutes for DOI and 4 hours for the deuterated compound of Example 1 (A1)), following which headshakes are recorded for 10 minutes using video cameras. The headshake response is a rapid, rhythmic shaking of the head in a radial motion. Data are analyzed by ANOVA followed by post hoc analysis where appropriate.

Dunnett's post analysis finds that, compared to vehicle, DOI significantly increases the number of headshakes. None of the doses of the deuterated compound of Example 1 (A1) have any significant effect on this measure.

Acute oral administration of the deuterated compound of Example 1 (A1) (1, 5, and 10 mg/kg) shows no significant increase in the number of headshakes compared to vehicle. DOI (3 mg/kg) significantly increases headshake responses in the rats following acute i.p. injection.

Example 11—DOI-Induced Headshake Response

Adult male Sprague Dawley rats are used. The deuterated compound of Example 1 (A1) (1, 5, and 10 mg/kg) is formulated in 0.5% methylcellulose solution and administered orally (PO) at a dose volume of 1 ml/kg 4 hours prior to test. DOI (3 mg/kg) is dissolved in saline and administered IP at a dose volume of 1 ml/kg (10 minutes prior to test). Ketanserin (1 mg/kg) is dissolved in saline and injected IP 30 minutes prior to DOI at a dose volume of 1 mg/kg.

Animals are administered vehicle, ketanserin, or test compound and returned to their holding cage for the appropriate pretreatment time (4 hours for the deuterated compound of Example 1 (A1) and 30 minutes for ketanserin). Rats are then injected with DOI and headshakes are recorded 10 minutes after DOI injection for 10 minutes using video cameras. The headshake response is a rapid, rhythmic shaking of the head in a radial motion. Data is analyzed by ANOVA followed by post hoc analysis where appropriate.

Dunnett's post analysis finds that, compared to vehicle, DOI significantly increases the number of headshakes. Ketanserin and the deuterated compound of Example 1 (A1) (5 and 10 mg/kg) decrease DOI-induced headshake responses. The deuterated compound of Example 1 (A1) at 1 mg/kg shows a non-significant trend to decreasing DOI-induced headshake responses ($p=0.051$, an effect is considered significant if $p<0.05$).

Acute oral administration of the deuterated compound of Example 1 (A1) (5 and 10 mg/kg) decreases DOI-induced headshakes compared to vehicle. The deuterated compound of Example 1 (A1) shows a trend to decreasing the DOI-induced headshake response. Ketanserin (1 mg/kg) also decreases the number of headshake responses induced by DOI following acute i.p. injection.

What is claimed:

1. A compound of Formula I:

Formula I

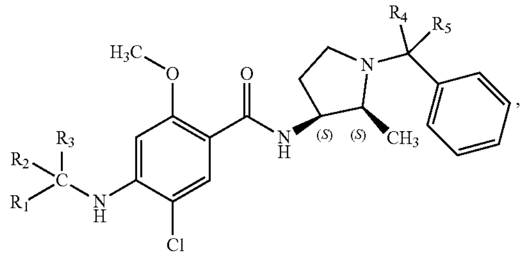

wherein:

$R_1$, $R_2$, $R_3$, $R_4$, and $R_5$ are independently selected from H and D; and at least one of $R_1$, $R_2$, and $R_3$ is D;

in free or salt form.

2. The compound according to claim 1, wherein the compound is in free form.

3. The compound according to claim 1, wherein $R_1$, $R_2$, and $R_3$ are D.

4. A compound, wherein the compound is:

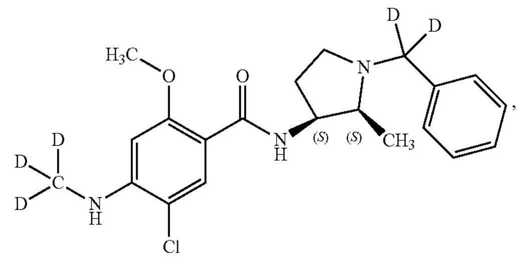

in free or pharmaceutically acceptable salt form.

5. The compound according to claim 1, wherein the compound, in free or pharmaceutically acceptable salt form, has greater than 90% incorporation of deuterium at one or more positions designated as deuterium.

6. A pharmaceutical composition, wherein the pharmaceutical composition comprises a compound according to claim 1, in free or pharmaceutically acceptable salt form, and a pharmaceutically acceptable carrier.

7. The compound according to claim 4, wherein the compound is in free form.

8. The compound according to claim 4, wherein the compound, in free or pharmaceutically acceptable salt form, has greater than 90% incorporation of deuterium at the positions designated as deuterium.

9. The compound according to claim 7, wherein the compound, in free form, has greater than 90% incorporation of deuterium at the positions designated as deuterium.

10. A pharmaceutical composition, wherein the pharmaceutical composition comprises the compound according to claim 4, in free or pharmaceutically acceptable salt form, and a pharmaceutically acceptable carrier.

11. A pharmaceutical composition, wherein the pharmaceutical composition comprises the compound according to claim 7, in free form, and a pharmaceutically acceptable carrier.

12. A pharmaceutical composition, wherein the pharmaceutical composition comprises the compound according to claim 8, in free or pharmaceutically acceptable salt form, and a pharmaceutically acceptable carrier.

13. A pharmaceutical composition, wherein the pharmaceutical composition comprises the compound according to claim 9, in free form, and a pharmaceutically acceptable carrier.

14. The compound according to claim 4, wherein the compound, in free or pharmaceutically acceptable salt form, has greater than 96% incorporation of deuterium at the positions designated as deuterium.

15. The compound according to claim 7, wherein the compound, in free form, has greater than 96% incorporation of deuterium at the positions designated as deuterium.

16. A pharmaceutical composition, wherein the pharmaceutical composition comprises the compound according to claim 14, in free or pharmaceutically acceptable salt form, and a pharmaceutically acceptable carrier.

17. A pharmaceutical composition, wherein the pharmaceutical composition comprises the compound according to claim 15, in free form, and a pharmaceutically acceptable carrier.

* * * * *